(12) United States Patent
Zamora et al.

(10) Patent No.: US 7,482,427 B2
(45) Date of Patent: Jan. 27, 2009

(54) POSITIVE MODULATOR OF BONE MORPHOGENIC PROTEIN-2

(75) Inventors: Paul O. Zamora, Gaithersburg, MD (US); Louis A. Pena, Poquott, NY (US); Xinhua Lin, Plainview, NY (US); Kazuyuki Takahashi, Germantown, MD (US)

(73) Assignees: BioSurface Engineering Technologies, Inc., College Park, MD (US); Brookhaven Science Associates, Upton, NY (US)

( * ) Notice: Subject to any disclaimer, the term of this patent is extended or adjusted under 35 U.S.C. 154(b) by 284 days.

(21) Appl. No.: 11/064,039

(22) Filed: Feb. 22, 2005

(65) Prior Publication Data

US 2005/0196425 A1    Sep. 8, 2005

Related U.S. Application Data

(63) Continuation-in-part of application No. 10/644,703, filed on Aug. 19, 2003, which is a continuation-in-part of application No. 10/224,268, filed on Aug. 20, 2002, now Pat. No. 7,166,574.

(60) Provisional application No. 60/547,012, filed on Feb. 20, 2004.

(51) Int. Cl.
  *C07K 5/00* (2006.01)
  *C12N 15/63* (2006.01)
  *A61K 38/19* (2006.01)
  *A61K 38/00* (2006.01)

(52) U.S. Cl. .............. 530/300; 530/397; 530/402; 514/12

(58) Field of Classification Search .............. None
See application file for complete search history.

(56) References Cited

U.S. PATENT DOCUMENTS

| | | |
|---|---|---|
| 4,172,128 A | 10/1979 | Thiele et al. |
| 4,563,350 A | 1/1986 | Nathan et al. |
| 5,563,046 A | 10/1996 | Mascarenhas et al. |
| 5,608,035 A | 3/1997 | Yanofsky et al. |
| 5,635,597 A | 6/1997 | Barrett et al. |
| 5,643,873 A | 7/1997 | Barrett et al. |
| 5,648,458 A | 7/1997 | Cwirla et al. |
| 5,654,276 A | 8/1997 | Barrett et al. |
| 5,668,110 A | 9/1997 | Barrett et al. |
| 5,674,977 A | 10/1997 | Gariepy |
| 5,679,637 A | 10/1997 | Lappi et al. |
| 5,679,673 A | 10/1997 | Bowen et al. |
| 5,687,136 A | 11/1997 | Godowski |
| 5,728,802 A | 3/1998 | Barrett et al. |
| 5,759,515 A | 6/1998 | Rhodes et al. |
| 5,767,234 A | 6/1998 | Yanofsky et al. |
| 5,770,704 A | 6/1998 | Godowski |
| 5,773,569 A | 6/1998 | Wrighton et al. |
| 5,786,322 A | 7/1998 | Barrett et al. |
| 5,786,331 A | 7/1998 | Barrett et al. |
| 5,789,182 A | 8/1998 | Yayon et al. |
| 5,830,851 A | 11/1998 | Wrighton et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,932,462 A | 8/1999 | Harris et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. |
| 6,011,002 A | 1/2000 | Pastan et al. |
| 6,030,812 A | 2/2000 | Bauer et al. |
| 6,051,648 A | 4/2000 | Rhee et al. |
| 6,121,236 A | 9/2000 | Ben-Sasson |
| 6,168,784 B1 | 1/2001 | Offord et al. |
| 6,174,530 B1 | 1/2001 | Rose et al. |
| 6,174,721 B1 | 1/2001 | Innis et al. |
| 6,214,795 B1 | 4/2001 | Benjamin et al. |
| 6,217,873 B1 | 4/2001 | Rose et al. |
| 6,235,716 B1 | 5/2001 | Ben-Sasson |

(Continued)

FOREIGN PATENT DOCUMENTS

| | | |
|---|---|---|
| WO | WO00/18921 | 4/2000 |
| WO | WO02/04015 | 1/2002 |
| WO | WO02/19963 | 3/2002 |
| WO | WO02/20033 | 3/2002 |
| WO | WO02/062823 | 8/2002 |

OTHER PUBLICATIONS

Kirsch et al., EMBO J., 2000, 19(13):3314-3324.*
Feeley et al., J. Bone Miner. Res., 2005, 20(12):2189-2199.*
Ahmed, Asif, et al., "Role of VEFGF Receptor-1 (Fit-1) in Mediating Calcium-Dependent Nitric Oxide Release and Limiting DNA Synthesis in Human Trophoblast Cells", *Lab Invet*, vol. 76(6), (1997),779-791.

(Continued)

*Primary Examiner*—Elizabeth C. Kemmerer
*Assistant Examiner*—Xiaozhen Xie
(74) *Attorney, Agent, or Firm*—Janeen Vilven; Stephen A. Slusher; Peacock Myers, P.C.

(57) ABSTRACT

Compounds of the present invention of formula I and formula II are disclosed in the specification and wherein the compounds are modulators of Bone Morphogenic Protein activity. Compounds are synthetic peptides having a non-growth factor heparin binding region, a linker, and sequences that bind specifically to a receptor for Bone Morphogenic Protein. Uses of compounds of the present invention in the treatment of bone lesions, degenerative joint disease and to enhance bone formation are disclosed.

8 Claims, 12 Drawing Sheets

U.S. PATENT DOCUMENTS

| | | |
|---|---|---|
| 6,251,864 B1 | 6/2001 | Dower et al. |
| 6,284,503 B1 | 9/2001 | Caldwell et al. |
| 6,294,359 B1 | 9/2001 | Fiddes et al. |
| 6,323,323 B1 | 11/2001 | Sledziewski et al. |
| 6,326,468 B1 | 12/2001 | Canne et al. |
| 6,342,591 B1 | 1/2002 | Zamora et al. |
| 6,350,731 B1 | 2/2002 | Jehanli et al. |
| 6,377,349 B1 | 4/2002 | Fercher |
| 6,451,543 B1 | 9/2002 | Kochendoerfer et al. |

OTHER PUBLICATIONS

Binetruy-Tournaire, Roselyne, et al., "Identification of a peptide blocking vascular endothelial growth factor (VEGF)-mediated angiogenesis", *The EMBO Journal*, vol. 19, (2000),1525-1533.

Dawson-Philip E., et al., "Synthesis of Native Proteins by Chemical Ligation", *Annu. Rev. Biochem.*, (2000),923-60.

Engstrom, Ulla, et al., "Identification of a Peptide Antagonist for Platelet-derived Growth Factor", *The Journal of Biological Chemistry*, vol. 273, (1998),15811-15817.

Gay, Cyril G., et al., "Interleukin 1 regulated heparin-binding growth factor 2 gene expression in vascular smooth muscle cells", *Proc. Natl. Acad. Sci. USA*, vol. 88, (Jan. 1991),296-300.

Hoke, David E., et al., "A heparin binding synthetic peptide from human HIP/RPL29 fails to specifically differentiate between anticoagulantly active and inactive species of heparin", *Journal of Negative Results in BioMedicine 2:1*, (2003).

Yoneda, Atsuko, "Engineering of an FGF-proteoglycan fusion protein with heparin-independent, mitogenic activity", *Nature Biotechnology* vol. 18, (Jun. 2000),641-644.

Brennand, David M. 1 "Identification of a Cyclic Peptide Inhibitor of Platelet-Derived Growth Factor-BB Receptor-Binding and Mitogen-Induced DNA Synthesis in Human Fibroblasts", *FEBS Letters*, 413 1997, 70-74.

Ostman, Arne 1 "Identification of Three Amino Acids in the Platelet-Derived Growth Factor (PDGF) B-chain that are Important for Binding to the PDGF B-Receptor", *The Journal of Biological Chemistry*, vol. 266, No. 16, Issue of June 5, 1991, 10073-10077.

Shen, Wei-Chiang 1 "Poly(I-lysine) has different membrane transport and drug-carrier properties when complexed with heparin", *Proc Natl Acad Sci USA* Dec. 1981, 7589-93.

Tanaka, H. 1 "Involvemenet of bone morphogenic protein-2 (BMP-2) in the pathological ossification process of the spinal ligament", *Rheumatology 2001*;40 May 9, 2001, 1163-1168.

\* cited by examiner

POSITIVE MODULATOR OF BONE MORPHOGENIC PROTEIN-2

CROSS-REFERENCE TO RELATED APPLICATIONS

This application is a continuation-in-part application of U.S. patent application Ser. No. 10/644,703, entitled Synthetic Heparin-Binding Growth Factor Analogs, filed on Aug. 19, 2003, which in turn is a continuation-in-part of U.S. Pat. Ser. No. 10/224,268, now U.S. Pat. No. 7,166,574 entitled Synthetic Heparin-Binding Growth Factor Analogs, filed on Aug. 20, 2002, and the specification thereof of each is incorporated herein by reference.

This application claims the benefit of the filing of U.S. Provisional Patent Application Ser. No. 60/547,012, entitled Positive Modulator of Bone Morphogenic Protein-2, filed on Feb. 20, 2004 and the specification thereof is incorporated herein by reference.

STATEMENT REGARDING FEDERALLY SPONSORED RESEARCH OR DEVELOPMENT

This invention was made with United States Government support under contract number DE-AC02-98CH10886, awarded by the U.S. Department of Energy. The United States Government has certain rights in the invention.

BACKGROUND OF THE INVENTION

1. Field of the Invention (Technical Field)

The present invention relates to synthetic growth factor modulator compositions, particularly modulators of the Bone Morphogenic Protein (BMP) family. Compositions of the present invention are of the formulas disclosed herein with a single or dual chain peptide sequence having specific binding affinity to a BMP-2 receptor, a linker, optionally a hydrophobic linker, and a non-growth factor heparin-binding sequence, and methods of use of synthetic growth factor modulators.

2. Background Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Bone Morphogenic Proteins (BMPs) are a group of proteins involved in the development of a wide range of organs and tissues from embryonic through adult stages, (Wozney J M 2002, *Spine* 27(16 Suppl 1):S2-8). BMPs also play important roles in tissue repair and remodeling processes following injuries. Certain BMPs induce ectopic bone formation and enhance healing of critical-sized segmental bone defects in animal models. Clinical studies show that recombinant human BMPs (rhBMPs) are safe and effective alternatives to autologous bone grafting. rhBMP-2 and rhBMP-7 are approved for human use in spinal fusion and recalcitrant long-bone nonunions, respectively. (Kleeman et al. 2001, *Spine* 26(24):2751-6. Burkus et al. 2002, *Spine* 27(21):2396-408. McKay et al. 2002, *Spine* 27(16 suppl 1):S66-85. Poynton et al. 2002, *Spine* 27(16 suppl 1):S40-8.)

The effectiveness of rhBMP-2 seems to heavily depend on the dose. Significantly higher-than-physiological doses are required for therapeutic effect in vivo. For example, levels in the neighborhood of 1 mg/mL of rhBMP-2 are used in spinal fusion cages (up to 8 mg/cage), an amount three orders of magnitude higher than what is typically found endogenously. (McKay et al. 2002, *Spine* 27(16 suppl 1):S66-85.) Administration of such a high dose of recombinant protein is not only costly, but may also be associated with adverse effects such as bony overgrowth and immunological reactions. Therefore, the development of positive modulators of BMP-2 to enhance BMP activities is of clinical significance.

BMP-2 signaling involves two types of transmembrane serine/threonine kinase receptors, namely type I (BRI) and type II (BRII). (Hoodless et al. 1996, *Cell* 85(4):489-500. Kawabata et al. 1995, *J Biol Chem* 270(10):5625-30. Nohno et al. 1995, *J Biol Chem* 270(38):22522-6. Rosenzweig et al. 1995, *Proc Natl Acad Sci USA* 92(17):7632-6.) An active ligand/receptor complex consists of BMP-2, BRI, and BRII in a 2:2:2 ratio. (Reddi A H 2001, *J Bone Joint Surg Am* 83-A Suppl 1(Pt 1):S1-6.) Both type I and type II receptors are required for BMP-2 to exert its biological functions. Upon BMP-2 binding, BRI kinase is activated as a result of phosphorylation by BRII. BRII would not bind to BMP-2 without the presence of BRI and the complex of BMP-2 and BRII is not capable of initiating signaling in the absence of BRI. The serine/threonine kinase in the BRI receptor is believed to be responsible for the phosphorylation of Smad1, Smad5, and Smad8, which in turn assemble into heteromeric complexes with Smad4 and translocate into the nucleus to regulate transcription of target genes. (Massague et al. 2000, *Genes Dev* 14(6):627-44. Attisano et al. 2000, *Curr Opin Cell Biol* 12(2):235-43.) In addition, the activated receptor complexes can activate the p38 MAP kinase pathway independent of the Smad pathway. (Iwasaki et al. 1999, *J Biol Chem* 274(37):26503-10. Miyazono K 2000, *J Cell Sci* 113(Pt 7):1101-9.) Currently there are thought to be two modes for BMP-2 to initiate signaling. Gilboa and colleagues showed that multiple BMP receptor oligomers are present at the cell surface prior to ligand binding. (Gilboa et al. 2000, *Mol Biol Cell* 11(3):1023-35.) Nohe and colleagues then showed that the pre-formed receptor complexes are responsible for the BMP-2 induced Smad pathway activation, and BMP-2-induced receptor complexes initiate the p38 kinase pathway. (Nohe et al. 2002, *J Biol Chem* 277(7):5330-8.)

Some efforts have been made to generate heparin-binding growth factor analogs. For example, natural platelet-derived growth factors (PDGF) occur as an A chain and a B chain arranged in head-to-head (M or BB) homodimers, or (AB or BA) heterodimers. Thus, U.S. Pat. No. 6,350,731 to Jehanli et al. discloses PDGF analogs in which two synthetic PDGF receptor-binding domains are covalently linked through a polyglycine or an N-(4-carboxy-cyclohexylmethyl)-maleimide (SMCC) chain to mimic the natural active polypeptide dimer.

U.S. Pat. No. 6,235,716 to Ben-Sasson discloses analogs of angiogenic factors. The analogs are branched multivalent ligands that include two or more angiogenic homology regions connected by a multilinker backbone.

U.S. Pat. No 5,770,704 (the '704 patent) to Godowski discloses conjugates for activating receptor tyrosine kinases, cytokine receptors and members of the nerve growth factor receptor superfamily. The conjugates include at least two ligands capable of binding to the cognate receptor, so that the binding of the respective ligands induces oligomerization of these receptors. The ligands disclosed in the '704 patent are linked by covalent attachment to various non-proteinaceous polymers, particularly hydrophilic polymers, such as polyvinylalcohol and polyvinylpyrrolidone, and the polyvinylalkene ethers, including polyethylene glycol and polypropylene glycol. The ligands include hepatocyte growth factor (HGF)

peptide variants that each bind HGF receptor, thereby causing receptor dimerization and activation of the biological activity of the HGF receptor dimer.

U.S. Pat. No. 6,284,503 (the '503 patent) to Caldwell et al. discloses a composition and method for regulating the adhesion of cells and biomolecules to hydrophobic surfaces and hydrophobic coated surfaces for cell adhesion, cell growth, cell sorting and biological assays. The composition is a biomolecule conjugated to a reactive end group activated polymer. The end group activated polymer includes a block copolymer surfactant backbone and an activation or reactive group. The block copolymer may be any surfactant having a hydrophobic region capable of adsorbing onto a hydrophobic surface, and a hydrophilic region which extends away from the surface when the hydrophobic region is adsorbed onto the hydrophobic surface. The '503 patent discloses that the biomolecules that may be conjugated to the end group activated polymer include natural or recombinant growth factors, such as PDGF, EGF, TGFα, TGFβ, NGF, IGF-I, IGF-II, GH and GHRF, as well as multi-CSF(II-3), GM-CSF, G-CSF, and M-CSF.

Other workers have described compositions that include homologs and analogs of fibroblast growth factors (FGFs). See for example U.S. Pat. No. 5,679,673 to Lappi and Baird; U.S. Pat. No. 5,989,866 to Deisher et al. and U.S. Pat. No. 6,294,359 to Fiddes et al. These disclosures relate to FGF homologs or analogs that are either conjugated to a toxic moiety and are targeted to the FGF receptor-bearing cells; or are homologs or analogs that modulate the biological pathways through the signal transduced by the FGF receptor upon binding by the FGF homolog or analog.

A series of patent applications to Kochendoerfer et al. disclose polymer-modified proteins, including synthetic chemokines and erythropoiesis stimulating proteins. See, for example, International Publications WO 02/04105, WO 02/19963 and WO 02/20033. These include chemically ligated peptide segments of a polypeptide chain of a synthetic erythropoiesis protein, such that a polypeptide chain results, with a water soluble polymer attached at one or more glycosylation sites on the protein. These applications also disclose synthetic chemokines, which are also polymer modified, and are asserted to be antagonists. However, heparin-binding domains are not disclosed. Other erythropoietin mimetics are known, such as those disclosed in U.S. Pat. Nos. 5,773,569 and 5,830,851 to Wrighton et al.

International Publication WO 00/18921 to Ballinger and Kavanaugh discloses a composition consisting of fusion proteins having FGF receptor affinity linked to an "oligomerization domain", either directly or through a linking group. The oligomerization domain ranges in length from about 20 to 300 residues, and includes constructs such as transcription factors, Fc portions of IgG, leucine zippers and the like. The oligomerization domains disclosed are homodimeric domains, wherein a single FGF receptor affinity fusion protein is linked to a single domain, such as a leucine zipper, which in turn is linked to a similar molecule by means of cysteine residues at both the amino and carboxy termini of the leucine zippers, such that two parallel leucine zippers, each with a single FGF receptor affinity fusion protein, are cross-linked by means of disulfide bonds. It is also disclosed that fusion proteins may include a heparin binding domain, such as the use of jun as a multimerization domain, which is asserted to be a heparin binding domain. Thus the compositions disclosed by Ballinger and Kavanaugh are all composed of a single receptor-binding sequence covalently attached to an oligomerization domain, whereby two or more similar oligomerization domains, each with a single receptor-binding sequence, are conjoined by means of either an association provided by the oligomerization domain, or alternatively, are chemically cross-linked to provide for the covalent bonding of the individual components.

The above described homologs, analogs, conjugates or ligands each include a receptor-binding domain. However, none of the disclosed compounds or compositions further include both a linker, providing for the linking of two receptor-binding domains to a dipeptide sequence, and further providing a single non-signaling peptide containing a heparin-binding domain. Moreover, none of these or other known heparin-binding growth factor analogs provide the advantages described herein below. Further, the prior art does not disclose modulators which, through a synergistic effect, increase or enhance the efficacy of a naturally occurring growth factor, such as BMP-2.

BRIEF SUMMARY OF THE INVENTION

Compounds of the present invention are partial agonists of bone morphogenic protein 2 (BMP-2), and particularly human BMP-2. As used herein, "BMP-2" includes specifically human BMP-2, but is not limited to human BMP-2. Compounds of the present invention substantially augment the bioactivity of BMP-2. Among other applications, compounds of the present invention can be employed as an additive to demineralized bone matrix (DBM) and bone graft materials to maximize the bioactivity of BMP-2. Compounds of the present invention augment the bioactivity of BMP-2 found in DBM (exogenous) and in bone undergoing repair (endogenous). Compounds of the present invention are preferably made by solid phase peptide chemistry. The clinical use of compounds of the present invention provide a new and novel treatment strategy applicable to accelerating bone repair, among other uses.

Compounds of the present invention substantially increase the bio-effectiveness of BMP-2 and significantly decrease the BMP-2 dose threshold. Compounds of the present invention plus BMP-2 result in significant increases of alkaline phosphatase (ALP) activity at sub-threshold concentrations of BMP-2. Compounds of the present invention interact directly with BMP receptor isoforms, and the combination of compounds of the present invention and BMP-2 causes a synergistic repression of mitogen-activated protein kinase (MAP kinase) and a synergistic increase of Smad activation. The synergistic increase of Smad activation is hypothesized to be largely responsible for the observed effect or action of these compounds on a system. Compounds of the present invention may be supplied with DBM, for example, with enhanced bone repair accordingly resulting from a) the augmentation BMP-2 found in DBM, and b) augmentation of host BMP-2 known to be unregulated in bone-repair. Similarly, if compounds of the present invention are supplied in concert with classic osteoconductive materials such as tricalcium phosphate or calcium sulfate, it can augment host BMP-2 and lead to osteoinduction and increased cellular migration into the bone fill material. Both approaches take advantage of the fact that BMP-2 and its receptors are up-regulated during bone repair processes.

One embodiment of the present invention is a compound of formula I:

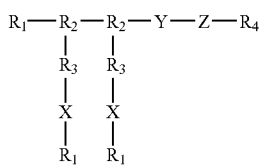

formula I wherein:
X is a peptide chain that (i) has a minimum of three amino acid residues, (ii) has a maximum of about fifty amino acid residues, and (iii) binds specifically to a Bone Morphogenic Protein-2 receptor;

$R_1$ is independently hydrogen, such that the terminal group is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is amino acid, a dipeptide or a tripeptide with an N-terminus $NH_2$, $NH_3^+$, or NH group;

$R_2$ is independently a trifunctional alpha amino acid residue, wherein X is covalently bonded through a side chain of $R_2$;

$R_3$ is independently a linker comprising a chain from 0 to about 15 backbone atoms covalently bonded to $R_2$;

$R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or NH—$R_1$;

Y is a linker comprising a chain from 0 to about 50 backbone atoms covalently bonded to $R_2$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids.

Yet another embodiment of the present invention is a bioactive implant containing a coating of formula I. Yet another embodiment of the present invention is a medicament for the therapeutic or prophylactic treatment of treat bone lesions or degenerative joint conditions made from formula I. Still another embodiment of the present invention is a compound of formula I used in a pharmaceutical composition and or a pharmaceutically acceptable salt thereof and a pharmaceutical carrier.

Another embodiment of the present invention is a compound of formula II

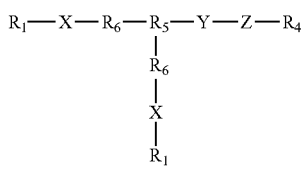

formula II wherein:
X is a peptide chain that (i) has a minimum of three amino acid residues, (ii) has a maximum of about fifty amino acid residues, and (iii) binds specifically to a Bone Morphogenic Protein-2 receptor;

$R_1$ is independently hydrogen, such that the terminal group is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is amino acid, a dipeptide or a tripeptide with an N-terminus $NH_2$, $NH_3^+$, or NH group;

$R_6$ is independently a linker comprising a chain from 0 to about 15 backbone atoms covalently bonded to $R_3$ when the linker is greater than 0 atoms;

$R_5$ is a trifunctional alpha amino acid residue, wherein X is covalently bonded through a side chain of $R_5$;

$R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or NH—$R_1$;

Y is a linker comprising a chain from 0 to about 50 backbone atoms covalently bonded to $R_5$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids.

Another embodiment of the present invention is a bioactive implant having at least one coating containing the compound of formula II.

Yet another embodiment of the present invention is a pharmaceutical composition containing the compound of formula II or a pharmaceutically acceptable salt thereof and a pharmaceutical carrier.

Yet another embodiment of the present invention is a method to enhance bone formation or to treat bone lesions or to treat degenerative joint conditions in a vertebrate animal, which method comprises administering to a vertebrate subject in need of such treatment an effective amount of a compound of formula I or formula II that augments Bone Morphogenic Protein-2 activity wherein the compound is a synthetic peptide having a non-growth factor heparin binding region, a linker and a sequence that binds specifically a to Bone Morphogenic Protein-2 Receptor.

One aspect of the present invention provides a synthetic growth factor modulator.

Another aspect of the present invention provides a compound that is a synthetic growth factor analog which is a positive modulator of BMP-2 activity in vivo.

Yet another aspect of the present invention provides a compound that is a positive modulator of BMP-2 activity in vitro.

Still another aspect of the present invention provides a compound that reduces the effective dose of exogenously applied BMP-2 for therapeutic purposes.

Another aspect of the present invention is to reduce the therapeutically effective dose of recombinant BMP delivered to a subject in need thereof.

Another aspect of the present invention provides a method for treating a subject having a bone injury, by providing a compound of the present invention in combination with a recombinant member of the BMP family to a fracture site.

Another aspect of the present invention provides a method for treating a subject having a bone injury, by providing a compound of the present invention to a fracture site.

Another aspect of the present invention provides a method for treating a subject in need of bone growth, by providing a compound of the present invention in combination with a recombinant member of the BMP family to a site in a subject in need of treatment.

Another aspect of the present invention provides a method for treating a subject in need of bone growth, by providing compound of the present invention to a site in a subject in need of treatment.

Another aspect of the present invention provides for kits containing a compound of the present invention.

Another aspect of the present invention provides for kits containing a composition of the present invention.

Another aspect of the present invention is a bioactive implantable device containing a compound of the present invention.

Other aspects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1A:
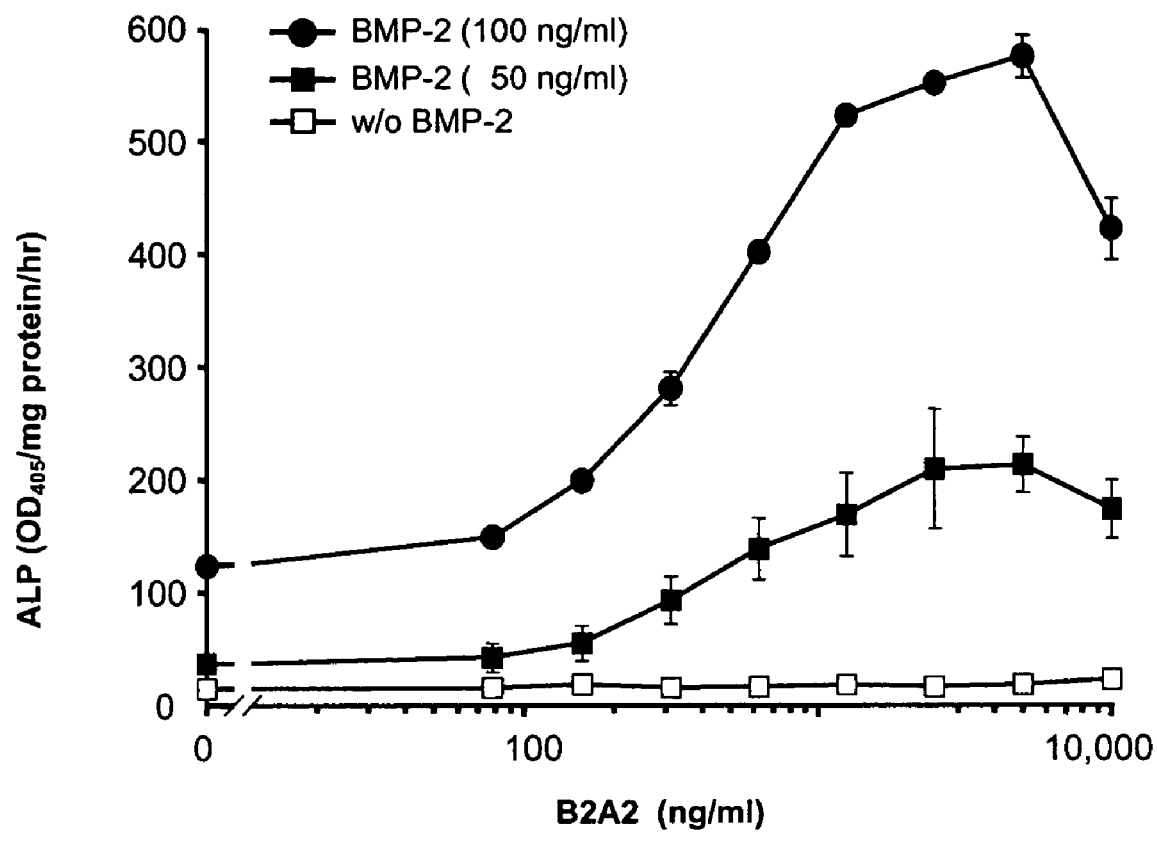
FIGS. 1A and 1B are graphs illustrating that B2A2 enhances BMP-2 induction of alkaline phosphatase (ALP) activity in C3H10T½ cells.

In a clinical setting, compounds of the present invention may be supplied with DBM, for example, with enhanced bone repair accordingly resulting from a) the augmentation BMP-2 found in DBM, and b) augmentation of host BMP-2 known to be upregulated in bone-repair. Similarly, if compounds of the present invention are supplied in concert with classic osteoconductive materials such as tricalcium phosphate, it can augment host BMP-2 and lead to osteoinduction and increased cellular migration into the bone fill material. Both approaches take advantage of the fact that BMP-2 and its receptors are up-regulated during bone repair processes.

In keeping with the known activation pathway of BMP-2, it is hypothesized that compounds of the present invention interact directly with BMP receptor isoforms (BRI and BRII), and that the combination of a compound of the present invention and BMP-2 causes a synergistic repression of mitogen-activated protein kinase (MAP kinase) and a synergistic increase of Smad activation compared to using BMP-2 alone. While BMP-2 inhibitors are known, these are the first known BMP-2 enhancers that functions in the physiological range.

Compounds of the present invention interact directly with BMP receptors to positively modulate BMP-2 induced events leading to osteogenic differentiation. Synergistic effects between compounds of the present invention and BMP-2 were observed in two multipotent cell lines, C3H10T½ and C2C12, as determined by at least two osteogenic differentiation markers, ALP activity and phosphorylation of Smad. The augmentation of ALP activity at any given concentration of BMP-2 was generally a 5-20 fold increase. While researchers have identified other BMP-2 modulators that have either been negative regulators or agents that fail to work under normal physiological conditions, compounds of the present invention are the first peptide specific regulators that positively modulate BMP-2.

Recently several BMP-specific antagonists have been identified. Noggin, chordin, and gremlin have been shown to bind to BMPs with the same affinity as BMP receptors, and thus competitively inhibit BMPs. (Zimmerman et al. 1996, *Cell* 86(4):599-606. Hsu et al. 1998, *Mol Cell* 1(5):673-83.) In a rat marrow cell culture, bFGF has been shown to act synergistically with BMP (Hanada et al. 1997, *J Bone Miner Res* 12(10):1606-14. Wang et al. 1993, *Acta Orthop Scand* 64(5):557-61.), however, higher doses of bFGF caused profound inhibitory effect in vivo. Spinella-Jaegle and colleagues reported that Sonic hedgehog (Shh) enhanced BMP-2 effects in C3H10T½ and ST2 cells, but it failed to enhance BMP-2 activity in analogous osteoprogenitor cells C2C1 2 and a preosteoblast cells MC3T3-E1. They further showed that the enhancing effect appeared to be a priming effect in which Shh increased the percentage of cells responding to BMP-2 (Spinella-Jaegle S, et al. 2001, *J Cell Sci* 114(Pt 11):2085-94), whereas Shh itself is able to induce ALP activity in C3H10T½. (Nakamura et al. 1997, *Biochem Biophys Res Commun* 237(2):465-9. Kinto et al. 1997 *FEBS Lett* 404(2-3):319-23. Katsuura et al. 1999, *FEBS Lett* 447(2-3): 325-8. Yuasa et al. 2002, *J Cell Physiol* 193(2):225-32.)

In another line of investigation, attempts to generate peptides that possess BMP activity have been less than satisfactory. Osteoinductive effects were reported by Dee and colleagues for a stretch of BMP-7 sequence (White et al. 2001, vol. BED-Vol. 50. *American Society of Mechanical Engineers, Snowbird, Utah*, pp 201-202.), and also by Suzuki & Tanihara for two overlapping stretches of BMP-2 sequence (Saito et al. 2003, *Biochim Biophys Acta* 1651(1-2):60-7. Suzuki et al. 2000, *J Biomed Mater Res* 50(3):405-9.). These results, however, were obtained in supranormal experimental systems with peptides at extremely high concentrations and/or covalently attached to a substrate that kept them in contact with cells for a period of weeks. For example, the linear peptide reported to have the highest BMP-2-like activity (Saito et al. 2003, *Biochim Biophys Acta* 1651(1-2):60-7.) works only at concentrations ~2,000 times higher than BMP-2—at this level it completely displaces BMP-2 from cell surface receptors and is thus a competitor of BMP-2.

In contrast to prior-art peptides, compounds of the present invention enhance the activity of BMP-2 and do so in a concentration range of BMP-2 that can be anticipated in physiological settings.

Different sources of BMPs present different attributes to consider for human applications. BMPs have been purified from bone, but with very low yields, and potential health risks associated with isolation from allogenic donor bone also limit clinical application of BMP from this source. Most of the BMP in clinical use is recombinant protein obtained from eukaryotic cell culture. Complications of post-translation modification and low yield result in a very high cost of these recombinant proteins. Moreover, the amounts required for efficacy in human applications turned out to be unexpectedly high (McKay et al. 2002, *Spine* 27(16 suppl 1):S66-85. Poynton et al. 2002, *Spine* 27(16 suppl 1):S40-8.).

A BMP-specific enhancer, such as that disclosed herein, has unique clinical significance. A BMP-2 enhancer may be used to reduce the amounts of BMP-2 required. This is of medical and practical significance because as a synthetic peptide, compounds of the present invention are (a) less expensive to produce, (b) vastly more chemically stable, and (c) easy to chemically modify for enhanced drug delivery. Biologically, there are also other advantages. For example, the process of spinal fusion involves a sequence of events associated with a temporal and spatial pattern of osteogenic-related gene expression. Morone and colleagues (Morone et al. 1998, *Clin Orthop* (351):252-65.) studied the expression of the mRNA of several BMPs in spinal fusion and found that BMP-2 and others were increased at different levels at different times. It is daunting to match exogenous application recombinant BMP-2 to the biologically optimal schedule. Similarly, BMPs can occur as homo- and heterodimers. A BMP enhancer may thus be effective by augmenting the natural endogenous expression of BMPs as they occur in situ.

Compounds of the present invention can thus be used to reduce the effective dose of recombinant BMP-2 on or associated with medical devices, to maximize the biological activity of biological preparations like demineralized bone matrix (DMB), and to augment the endogenous levels of BMP-2 generated by host tissue during bone healing process.

DBM is one alternative material that is bone-derived and widely used in clinical practice. DBM is processed from human bone via solvent and acid treatments, and in its final form contains collagens and low levels of growth factors. DBM is available from a number of companies and organizations, including Wright Medical Technologies, Osteotech, the American Red Cross, and Innova. DBM, via the collagen component, provides a scaffold on which new bone forms and it also has some osteoinductive potential via its low levels of growth factors. It may also elicit some activation of mesenchymal stem cells from the surrounding area that differentiate into osteoblasts.

The osteoinductive potential of DBM is low, however, and varies widely from lot-to-lot and manufacturer-to-manufacturer. Since the growth factors in DBM are expected to have their most pronounced effect on osteoprogenitor cells, the availability of osteoprogenitor cells is critical when demineralized bone matrix is used. The limited ability of DBM to elicit a robust osteoinduction is widely seen as a limiting factor in the use of this material.

Among the calcium-rich bone graft materials, there are a large number of commercially available products bone filler agents that are not derived from human sources, including Pro Osteon™ (coralline hydroxyappatite, Interpore Cross International), Bioglass™ (bioactive glass implant, US Biomaterials Corp.), Collagraft™ (hydroxyapatite/tricalcium phosphate and pure bovine fibrillar collagen, Zimmer), Cellplex™ (tricalcium phosphate, synthetic cancellous bone, Wright Medical Technologies, Inc.), and a number of calcium phosphate and calcium phosphate fillers. All of these materials are osteoconductive and support the in-growth of capillaries, perivascular tissues, and osteoprogenitor cells from a host into an implant or graft. They are not, however, osteoinductive.

Among the biologics, a number of companies have developed bone fill products that are intended to be used with autologous bone marrow cells or platelet concentrates. These products are intended to increase the number of stem cells in a graft or to increase the amount of growth factors, respectively.

In a related vein, the InFuse™ spinal cage product (Sofamor-Danek, a division of Medtronic) is an example of a device that combines a osteoconductive material (collagen) with an osteoinductive agent. InFuse™ is indicated for use in conjunction with spinal fusion procedures, and a similar product is being developed for fresh fracture repair.

The success of InFuse™, and to a lesser extent, Stryker Corporation's OP-1 for use in tibial non-unions, has led to a high level of interest in recombinant growth factor approaches. Numerous additional growth factors are being evaluated in the orthopedic and ortho-biologic fields. Yet among the various BMPs, BMP-2 appears to be the factor with the highest degree of osteoinduction.

There is thus an increasing clinical demand for bone graft materials and a high level of interest in alternatives to growth factors or improvements in existing bone graft materials.

Definitions

As used here and elsewhere, the following terms have the meanings given.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "amide" includes compounds that have a trivalent nitrogen attached to a carbonyl group (—$CO.NH_2$).

An "amine" includes compounds that contain an amino group (—$NH_2$).

A "diamine amino acid" is an amino acid or residue containing two reactive amine groups and a reactive carboxyl group. Representative examples include 2,3 diamino propionyl amino acid, 2,4 diamino butylic amino acid, lysine or ornithine.

A "trifunctional amino acid" is an amino acid or residue with three reactive groups, one the N-terminus amine, a second the C-terminus carboxyl, and the third comprising all or a part of the side chain. Trifunctional amino acids thus include, by way of example only, diamine amino acids; amino acids with a reactive sulfhydryl group in the side chain, such as mercapto amino acids including cysteine, penicillamine, or 3-mercapto phenylalanine; amino acids with a reactive carboxyl group in the side chain, such as aspartic acid and glutamic acid; and amino acids with a reactive guanadium group in the side chain, such as arginine.

Compounds of the Present Invention

According to one embodiment of the present invention, compounds are of formula I:

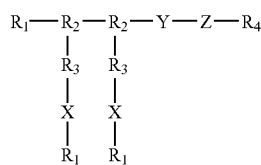

I wherein:

X is a peptide chain that (i) has a minimum of three amino acid residues, (ii) has a maximum of about fifty amino acid residues, and (iii) binds specifically to Bone Morphogenic Protein-2 receptor;

$R_1$ is independently a hydrogen, such that the terminal group is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is amino acid, a dipeptide or a tripeptide with an N-terminus $NH_2$, $NH_3^+$, or NH group;

$R_2$ is independently a trifunctional amino acid residue, wherein X is covalently bonded through a side chain of $R_2$;

$R_3$ is independently a linker comprising a chain from 0 to about 15 backbone atoms covalently bonded to $R_2$;

$R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or NH—$R_1$;

Y is a linker comprising a chain from 0 to about 50 backbone atoms covalently bonded to $R_2$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids.

According to another embodiment of the present invention compounds are of formula II:

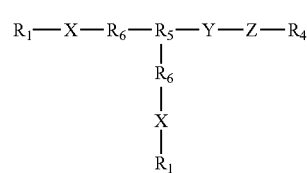

II wherein:

X is a peptide chain that (i) has a minimum of three amino acid residues, (ii) has a maximum of about fifty amino acid residues, and (iii) binds specifically to Bone Morphogenic Protein-2 receptor;

$R_1$ is independently a hydrogen, such that the terminal group is $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or is amino acid, a dipeptide or a tripeptide with an N-terminus $NH_2$, $NH_3^+$, or NH group;

$R_6$ is independently a linker comprising a chain from 0 to about 15 backbone atoms covalently bonded to $R_5$;

$R_5$ is a trifunctional amino acid residue, wherein a first X is covalently bonded through a side chain of $R_5$ and a second X is covalently bonded through the N-terminus amine;

$R_4$ is OH such that the terminal group is a carboxyl, $NH_2$, an acyl group with a linear or branched $C_1$ to $C_{17}$ alkyl, aryl, heteroaryl, alkene, alkenyl or aralkyl chain including an N-terminus $NH_2$, $NH_3^+$, or NH group or a corresponding acylated derivative, or NH—$R_1$;

Y is a linker comprising a chain from 0 to about 50 atoms covalently bonded to $R_2$ and Z; and Z is a non-signaling peptide chain that includes a heparin binding domain comprising an amino acid sequence that comprises (i) a minimum of one heparin binding motif, (ii) a maximum of about ten heparin binding motifs, and (iii) a maximum of about thirty amino acids.

In each of formula I and formula II, the covalent bonds can be, for example, a peptide bond or other amide bond, a thioether bond or ester bond. A group is covalently bonded to another group when it is, directly or through one or more other groups or atoms comprising covalent bonds, covalently bonded.

The chain of atoms of the Y region of formula I is covalently attached to $R_2$ and to sequence Z, and in formula II the Y region is covalently attached to $R_5$ and to sequence Z. The covalent bonds can be, for example, peptide, amide, thioether or ester bonds. Particularly preferred is a peptide bond. Preferably, the Y region includes a chain of a minimum of about nine backbone atoms. More preferably, the Y region includes a chain of a minimum of about twelve backbone atoms. Most preferably, the Y region includes a chain of a minimum of about fifteen backbone atoms. For example, the Y region may be formed from a chain of at least four, at least five or at least six amino acids. Alternatively, the Y region may be formed from a chain of at least one, at least two, or at least three amino carboxylic acids, such as aminohexanoic acid residues. Particularly preferred are embodiments in which Y is one or more straight chain amino carboxylic acids, such as where Y comprises $[NH_2-(CH_2)_pCO]_q$ wherein p is from 1 to about 10 and q is from 1 to about 20. Examples of straight chain amino carboxylic acids that may be employed include 6-aminohexanoic acid, 7-aminoheptanoic acid, 9-aminononanoic acid and the like.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For example, the Y region may be formed from a chain of up to about twelve, up to about fifteen, or up to about seventeen amino acids.

The amino acid sequence of the Y region is preferably an artificial sequence, i.e. it does not include any amino acid sequence of four or more amino acid residues found in a natural ligand of a BMP receptor.

In a particular embodiment, the Y region includes a hydrophobic amino acid residue, or a chain of hydrophobic amino acid residues. The Y region can, for example, include one or more amino carboxylic acid residues, such as one, two, three or more aminohexanoic acid residues. In another alternative embodiment, the Y region can include a combination of amino acid hydrophobic residues.

In another particular embodiment, the Y region of the molecule can include a branched or unbranched, saturated or unsaturated alkyl chain of between one and about twenty carbon atoms. In a further embodiment, the Y region can include a chain of hydrophilic residues, such as for instance, ethylene glycol residues. For instance, the Y region can include at least about three, or at least about four, or at least about five ethylene glycol residues.

The Z region of the molecule of formula I and formula II is a heparin-binding region and can include one or more heparin-binding motifs, BBxB or BBBxxB as described by Verrecchio et al. J. Biol. Chem. 275:7701 (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR] (SEQ ID NO:1), designating the first three amino acids as each independently selected from lysine or arginine, followed by any two amino acids and a sixth amino acid which is lysine or arginine.

The number of heparin-binding motifs is variable. For instance, the Z region may include at least one, at least two, at least three or up to at least five heparin-binding motifs. Where there are more than one heparin-binding motifs, the motifs may be the same or different. Alternatively, the Z region includes up to a maximum of about ten heparin-binding motifs. In another alternative embodiment, the Z region includes at least four, at least six or at least eight amino acid residues. Further, in certain embodiments the Z region includes up to about twenty, up to about twenty-five, or up to about thirty amino acid residues. It is to be realized that, in part, the avidity of the Z region for heparin is determined by the particular heparin-binding motifs selected and the number of such motifs in Z. Thus for particular applications both the selection and number of such motifs may be varied to provide optimal heparin binding of the Z region.

In a preferred embodiment, the amino acid sequence of the Z region is RKRKLERIAR (SEQ ID NO:2). In another embodiment, the amino acid sequence of the Z region is RKRKLGRIAR (SEQ ID NO:3). In yet another embodiment, the amino acid sequence of the Z region is RKRKLWRARA (SEQ ID NO:4). In yet another embodiment, the amino acid sequence of the Z region is RKRLDRIAR (SEQ ID NO:5), providing a heparin-binding motif derived from a modification of the sequence at residues 270-279 of the Jun/AP-1 DNA binding domain (Busch et al. Trans-Repressor Activity of Nuclear Glycosaminoglycans on Fos and Jun/AP-1 Oncoprotein-mediated Transcription. J. Cell Biol. 116:31-42, 1992). In yet another embodiment, the amino acid sequence of the Z region is RKRKLERIARC (SEQ ID NO:6). The presence of a terminal cysteine residue optionally affords the opportunity to link other molecules, including detection reagents such as fluorochromes, radioisotopes and other detectable markers, to the Z region, as well as the opportunity to link toxins, immunogens and the like.

The synthetic bone morphogenic protein analogs of the present invention, including those of formulas I and II, include embodiments wherein the X region is all or a portion, or a homolog of all or a portion, of any of the following amino acid sequences:

```
AISMLYLDENEKVVL              (SEQ ID NO:7)

ISMLYLDENEKVVLKNY,           (SEQ ID NO:8)

LYFDESSNVILKK,               (SEQ ID NO:9)

LYVDFSDVGWNDW,               (SEQ ID NO:10)

EKVVLKNYQDMVVEG,             (SEQ ID NO:11)

CAISMLYLDENEKVVL,            (SEQ ID NO:12)

AFYCHGECPFPLADHL,            (SEQ ID NO:13)

PFPLADHLNSTNHAIVQTLVNSV,     (SEQ ID NO:14)
or
```

In a preferred embodiment the X region is the amino acid sequence ISMLYLDENEKVVLKNY (SEQ ID NO:8). More preferably the X region is the amino acid sequence LYFDESSNVILKK (SEQ ID NO:9). More preferably still, the X region is the amino acid sequence AISMLYLDENEKVVL (SEQ ID NO:7).

The inventors have surprisingly and advantageously found that in the compounds of the present invention, including those of formulas I and II, the X region may be synthesized in a reverse direction, such that considering the sequence AISMLYLDENEKVVL (SEQ ID NO:7) illustrated in the conventional N→C orientation, and using formula I, the first amino acid bound to the $R_2$ side chains is the N-terminus amino acid residue, the second amino acid bound to the N-terminus amino acid residue is the 2 position residue, and so on, and the compounds nonetheless retain biological activity and specifically bind to a BMP receptor. It may be seen that such a construct has, based on a conventional N→C orientation, a reverse sequence, in that it is the carboxyl group of the conventional N-terminus amino acid residue that forms a peptide bond with the epsilon amine where $R_2$ is a diamine amino acid. Thus again employing a conventional N→C orientation, the foregoing sequences may be employed in a reverse orientation, and the resulting compound of present invention is biologically active and may be employed as described herein. According to a preferred embodiment, the X region is the sequence LVVKENEDLYLMSIA (SEQ ID NO:15) (again considering the sequence in the conventional N→C orientation), as disclosed in Example 2 herein. As described in Example 2, the C-terminus alanine (A) is bound to the epsilon amine of a lysine (K) in the $R_2$ position of formula I, the isoleucine (I) is bound by a peptide bond to the alanine, and so on. Thus the following sequence is provided, and is biologically active, as described herein:

stood that the X sequence need not be identical to all or a portion of a sequence listed below, and may be homologous with all or a portion, such as a sequence that is 80% to 95% homologous.-*

TABLE 1

| CYTOKINE | PREFERRED X RECEPTOR BINDING DOMAIN | |
|---|---|---|
| TGF-β1 | IVYYVGRKPKVEQLSNMIVRS | (SEQ ID NO:23) |
| TGF-β2 | TILYYIGKTPKIEQLSNMIVKS | (SEQ ID NO:24) |
| TGF-β3 | LTILYYVGRTPKVEQLSNMVV | (SEQ ID NO:25) |
| BMP-2 | AISMLYLDENEKVVLKNYQDMVV | (SEQ ID NO:26) |

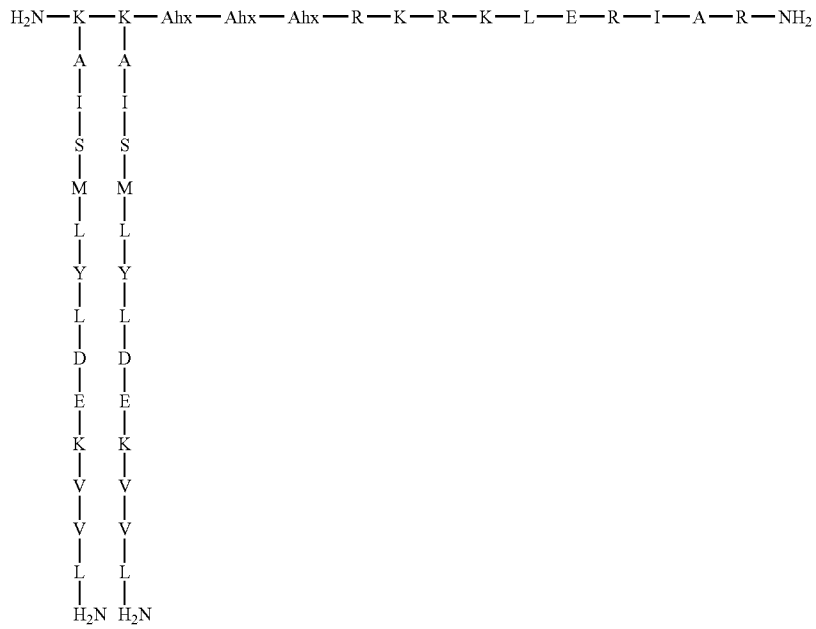

Other reverse sequences that may be employed, in whole or in part, including homologs thereto, in addition to LVVKENEDLYLMSIA (SEQ ID NO:15), include but are not limited to YNKLVVKENEDLYLMSI (SEQ ID NO:16), KKLIVNSSEDFYL (SEQ ID NO:17), WDNWGVDSFD-VYL (SEQ ID NO:18), GEVVMDQYNKLVVKE (SEQ ID NO:19), LHDALPFPCEGHCYFA (SEQ ID NO:20), VSN-VLTQVIAHNTSNLHDALPFP (SEQ ID NO:21), and LVVKENEDLYLMSIAC (SEQ ID NO:22).

Alternatively, in another particular aspect the invention provides synthetic BMP, TGF or GDF (growth differentiation factor) peptide analogs with sequences as shown in Table 1 wherein the transforming growth factor family member peptides are particularly useful in augmenting the activity of endogenous or artificial BMP peptides or TGF peptides, wherein is shown (under the heading "preferred X receptor binding domain") the sequence forming all or part of the X region of constructs of any of formulas I or II. It is to be understood that some or only a portion of any sequence listed under the heading "preferred X receptor binding domain" may be employed, and thus the X region employed may be a subset of any sequence listed below. It is further to be under- TABLE 1-continued

| CYTOKINE | PREFERRED X RECEPTOR BINDING DOMAIN | |
|---|---|---|
| BMP-3 | SSLSILFFDENKNVVLKVYPNMTV | (SEQ ID NO:27) |
| BMP-3β | NSLGVLFLDENRNVVLKVYPNMSV | (SEQ ID NO:28) |
| BMP-4 | AISMLYLDEYDKVVLKNYQEMVV | (SEQ ID NO:29) |
| BMP-5 | AISVLYFDDSSNVILKKYRNMVV | (SEQ ID NO:30) |
| BMP-6 | AISVLYFDDNSNVILKKYRNMVV | (SEQ ID NO:31) |
| BMP-7 | AISVLYFDDSSNVILKKYRNMVV | (SEQ ID NO:32) |
| BMP-8 | ATSVLYYDSSNNVILRKARNMVV | (SEQ ID NO:33) |
| BMP-9 | ISVLYKDDMGVPTLKYHYEGMSV | (SEQ ID NO:34) |
| BMP-10 | ISILYLDKGVVTYKFKYEGMAV | (SEQ ID NO:35) |
| BMP-11 | INMLYFNDKQQIIYGKIPGMVV | (SEQ ID NO:36) |
| BMP-12 | ISILYIDAANNVVYKQYEDMVV | (SEQ ID NO:37) |

TABLE 1-continued

| CYTOKINE | PREFERRED X RECEPTOR BINDING DOMAIN | |
|---|---|---|
| BMP-13 | ISILYIDAGNNVVYKQYEDMVV | (SEQ ID NO:38) |
| BMP-14 | ISILFIDSANNVVYKQYEDMVV | (SEQ ID NO:39) |
| BMP-15 | ISVLMIEANGSILYKEYEGMIA | (SEQ ID NO:40) |
| GDF-1 | ISVLFFDNSDNVVLRQYEDMVV | (SEQ ID NO:41) |
| GDF-3 | ISMLYQDNNDNVILRHYEDMVV | (SEQ ID NO:42) |
| GDF-8 | INMYLFNGKEQIIYGKIPAMVV | (SEQ ID NO:43) |
| GDF-9 | LSVLTIEPDGSIAYKEYEDMIA | (SEQ ID NO:44) |

The term "homologous", as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, or 20% of the amino acid residues when the amino acid sequences of the two peptide homologs are aligned.

Particularly useful amino acid sequences as X regions of formulas I or II include homologs of fragments of naturally occurring sequences that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another amino acid of the same acidic or basic character.

The $R_3$ regions of formula I or the $R_6$ regions of formula II can include a chain of atoms or a combination of atoms that form a chain. Typically, the chains are chains primarily of carbon atoms, that may also optionally include oxygen or nitrogen atoms, such as for example chains of atoms formed from amino acids (e.g. amino acids found in proteins, as listed above; naturally occurring amino acids not found in proteins, such as ornithine and citrulline; or non-natural amino acids, such as aminohexanoic acid; or a combination of any of the foregoing amino acids). It is also contemplated that agents such as polyethylene glycol (PEG), polyethylene oxide (PEO), amino polyethylene glycol, bis-amine-PEG, and other variants of polyethylene glycol known to those skilled in the art can similarly be used. Particularly preferred for the $R_3$ or $R_6$ regions are chains which include an amino terminal and a carboxyl terminal, such that the chains may be utilized in standard peptide synthesis methodologies. Examples include any amino acids, amino carboxylic acids, preferably straight chain amino carboxylic acids, and bifunctional amino-PEG-acid spacers. Among amino acids, glycine is preferred.

In certain embodiments of the invention, each of the $R_3$ regions of formula I or each of the $R_6$ regions of formula II can be different, although in most embodiments it is preferred that the regions be identical. However, it is contemplated that such regions may differ; for example, in formula II the $R_5$ may be a diamine amino acid, such as lysine. It is possible to utilize an orthogonal protecting group during synthesis to protect either the alpha amine or epsilon amine, to thereafter add one or amino acid residues or other groups to form an $R_6$ group, and then to remove the orthogonal protecting group, and proceed with parallel synthesis of the X groups from the deprotected amine on $R_5$ and the terminal amine on $R_6$. Similar methods may be employed with formula I.

Methods of Synthesizing the Compounds of the Present Invention

The synthesis of the compounds of the present invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The compounds of the present invention can be produced by stepwise synthesis or by synthesis of a series of fragments that can be coupled by similar well known techniques. See, for instance, Nyfeler, Peptide synthesis via fragment condensation. Methods Mol. Biol. 35:303-16 (1994); and Merrifield, Concept and early development of solid-phase peptide synthesis. Methods in Enzymol. 289:3-13 (1997). These methods are routinely used for the preparation of individual peptides. It is possible to assemble the analogs of the present invention in component parts, such as peptides constituting the X, Y and Z components thereof, and to thereafter couple such component parts to assemble the analog. See, for instance, Dawson and Kent, Synthesis of native proteins by chemical ligation. Annu. Rev. Biochem. 69:923-960 (2000); and Eom et al., Tandem ligation of multipartite peptides with cell-permeable activity. J. Am. Chem. Soc. 125:73-82 (2003). However, in a preferred embodiment the compounds of the present invention are synthesized by solid phase synthesis, with the C-terminus residue of the Z region of formulas I or II bound to resin, and the synthesis proceeding stepwise. Conventional protecting groups are employed as required, with deprotection either prior to, during or following cleavage of the peptide from the resin. By way of example only, for compounds of the present invention containing one or more lysine residues in addition to any at the $R_2$ position of formula I or the $R_5$ position of formula II, such additional lysine residues are conventionally protected with a protecting group, and deprotected following synthesis.

Methods of Use of the Compounds of the Present Invention

The compounds of the present invention provide a cost effective source of biologically active molecules that are useful in a number of ways, including as soluble prophylactic or therapeutic pharmaceutical agents.

The compounds of the present invention are also useful as biologically active agents as components of medical devices and for coating of medical devices, such as for instance, sutures, implants and medical instruments to promote biological responses, for instance, to stimulate growth and proliferation of cells, or healing of wounds.

In one aspect, the invention provides a method and compositions for treating a mammal with bone injury, by providing a compounds of the present invention, such as an analog of BMP-2. For example, such compounds of the present invention may be administered as a pharmaceutical agent, or may be employed as an additive to bone matrix or bone graft materials.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, aneurism coils, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, embolization particles, microbeads, dental implants, bone prostheses, bone graft materials, spinal fusion cages, bone fillers, orthopedic devices, tissue scaffolds, artificial joints or controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al. in U.S. Pat. No. 6,342,591 teach an amphipathic coating for medical devices for modulating cellular adhesion composition, and is incorporated herein by reference.

The compounds of the present invention can be used for as an active ingredient in pharmaceutical compositions for both medical applications and animal husbandry or veterinary applications. Typically, the compound of the present invention or pharmaceutical composition is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The compounds of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compounds of the present invention are basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the compounds of the present invention are prepared in a suitable solvent for the compound and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the compounds of the present invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a compounds of the present invention and a pharmaceutically acceptable carrier. The carrier may be a liquid formulation, and in one embodiment a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Thus the compounds of the present invention may be formulated or compounded into pharmaceutical compositions that include at least one compounds of the present invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, PEG, PEO, mannitol, sodium chloride or sodium citrate, as well as any number of simple sugars, including sucrose, dextrose, lactose and the like, and combinations of the foregoing. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compounds of the present invention over a period of time.

In practical use, the compounds of the present invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The invention is further illustrated by the following non-limiting examples.

EXAMPLE 1

Materials. C2C12 cells and C3H10T½ cells were purchased from American Type Culture Collection (Manassas, Va.). E. coli or Chinese hamster ovary (CHO) cell-derived recombinant human BMP-2 were purchased from R&D Systems (Minneapolis, Minn.). Soluble BMP-2 receptors as the recombinant BR1-Fc chimeric proteins were also obtained from R&D Systems. Endostatin-Fc, FGF-2, and VRGF were supplied by through the Biological Resources Branch of Developmental Therapeutics Program, National Cancer Institute. TGF-beta1 was purchased from Sigma Aldrich Chemical Company. Bovine serum albumin (BSA), anti-phosphorylated MAP kinase antibody, and anti-human Fc antibody conjugated to horseradish peroxidase were from Sigma (St. Louis, Mo.). Fetal bovine serum (FBS), calf bovine serum (CBS), DMEM/F12 medium, and penicillin/streptomycin were purchased from Invitrogen (Carlsbad, Calif.). Silyl-heparin is benzyl-tetra(dimethylsilylmethyl) oxycarbamoyl-heparin and was synthesized as detailed elsewhere (Zamora et al. 2002, Bioconjug Chem 13(5):920-6.). In brief, silyl-heparin is made by reacting the hydrophobic group benzyl-tetra(dimethylsilylmethyl)-oxycarbamoyl-succinimide with heparin thereby resulting in an amphipathic heparin derivative that can be adsorbed onto hydrophobic surfaces. For coating purposes, silyl-heparin was used as a 1% solution in 70% acidified, aqueous ethanol.

Alkaline phosphatase (ALP) Activity Assay. C2C12 cells and C3H10T½ cells were cultured at 37° C. in a humidified atmosphere of 5% $CO_2$ and 95% air, with DMEM/F12 medium supplemented with 10% serum, penicillin/streptomycin. For the BMP-2 induced ALP assay, cells were plated in 96-well ($1\times10^4$/well) dishes in regular growth medium. Twenty-four hours later, when the cells formed a confluent monolayer, medium was replaced with DMEM/F12, supplemented with 2% serum and containing indicated concentration of BMP-2 and/or B2A2. At 4-5 days post induction, ALP activity was determined as described by Akiyama and colleagues (Akiyama et al. 1997, Exp Cell Res 235(2):362-9.) with modifications. Briefly, cells were washed once with phosphate-buffered saline (PBS) and lysed with 0.1% Triton× 100 in 10 mM Tris HCl, pH 9.0. Protein concentration was determined using the BCA Protein Assay Kit (Pierce Biotechnology, Rockford, Ill.). Then ALP activity was measured by adding ALP buffer (1 M diethanolamine, 0.5 mM $MgCl_2$, 1 mg/mL p-nitrophenylphosphate, pH 9.0), incubating in 37° C., and absorbance (405 nm) read at 15, 30 and 60 minutes using a microplate spectrophotometer (Molecular Devices, Sunnyvale, Calif.). The activity was expressed as O.D. per mg protein per hour.

Peptide synthesis and preparation. The peptides B2A2 and B2A2-K-NS were synthesized by conventional solid phase synthesis and purified by reverse phase HPLC on C-18, as described in Example 2 and 9.

Fractions of HPLC purified peptide were pooled, lyophilized, and stored frozen. Aliquots of the lyophilized bulk material were used to determine the peptide content, which was determined using a commercially available kit (BCA, Pierce Endogen, Inc.). For most further purposes, the peptide was dissolved in 5.5% glucose containing 0.05% Pluronic 127 to a final concentration of 0.5 mg/mL or 1 mg/mL, sterilize filtered through a 0.22 micron filter, and lyophilized in aliquots containing 50 or 100 μg.

Receptor binding assays. Binding to BMP receptors in a solid phase binding assay. B2A2 was absorbed onto ELISA plates to saturation, soluble BMP receptor-immunoglobin Fc fusion proteins were added, and bound receptor was detected by HRP-conjugated anti-Fc antibody and colorimetric assay, values shown are background substracted. Specific binding of B2A2 to different receptor isoforms of the BMPR and Activin Receptor family were tested, employing the receptor-Fc chimeras shown. Negative controls establishing specificity included unrelated polypeptide (e.g. insulin) adsorbed to the plates, and incubation of unrelated chimeric protein (Endostatin-Fc), neither of which resulted in binding of B2A2. Apparent two stage binding to BMPR-Ib was revealed by receptor displacement experiments. Bound receptor was displaced by the addition of rhBMP-2 at the levels indicated.

Cell growth. L6 rat skeletal myoblasts and cells from a human fetal osteoblast cell line (hFOB) (5) were used as target. Aliquots of cells ($1-5\times10^3$ cells) were seeded into wells of 96 well plates and allowed to attach for 6-24 hours. The medium was replaced with serum low (2%) medium containing peptide. Paclitaxel (100 ng/mL) and sodium azide (0.01%), if used, were included as reference materials known to induce cytotoxicity. Cultures were incubated typically for 3 days after which time the relative cell number was assessed using the tetrazolium salt MTS.

Cell migration. For studies involving migration across a wound margin, the cells were grown in vitro and used when approximately 90% confluent. A simulated wound was made by scraping cells away from the cultureware surface. The cultures were rinsed to remove unbound cells, and then incubated in DMEM:F12 medium containing 2% newborn calf serum with or without peptide. FGF-2 (50 ng/mL) was used as a positive control reference material. The cells were allowed to migrate for 6 hours after which the cells were fixed in buffered formalin. Migration was monitored via phase contrast microscopy. Migrating cells were those that had migrated across the site of the simulated wound margin.

In vivo Matrigel™ plug assay. The in vivo model involved subcutaneous implant in young adult Fisher 344 of growth factor-reduced Matrigel with and without BMP-2 and B2A2. Animals were anesthetized before all procedures by intra peritoneal injections of ketamine (50 mg/kg) and xylazine (5 mg/kg). Growth factor reduced Matrigel™ at 4° C. (liquid state) was mixed with saline (control), BMP-2 (R&D Systems, Minneapolis, Minn.), B2A2-K-NS, or B2A2-K-NS plus BMP-2. Aliquots of 0.5 mL of Matrigel™ with additives as above were injected subcutaneously on the upper flanks of the rats. The injection sites were clipped with stainless steel clips to prevent leakage. The Matrigel™ was kept on ice until the time of injection, as were the needle and syringe (to prevent gelling in the needle). The animals were subsequently euthanized after 14 days, the gel surgically removed, measured with calipers, and fixed in buffered formalin. Most of the explants had a generally elliptical shape and the surface area of the ellipse was determined using the equation:

Area =πab where a and b are ½ the width and height of the ellipse.

The fixed specimens were processed for histological examination and stained with either hemotoxylin and eosin or toluidine blue O (Histoserv, Inc., Germantown, Md.).

EXAMPLE 2

A compound of the present invention was synthesized by solid phase peptide chemistry with the general structure of formula I wherein X is a BMP-2 receptor binding amino acid sequence having the sequence AISMLYLDEKVVL (SEQ ID NO:7) wherein SEQ ID NO:7 was stepwise synthesized in parallel from $R_2$ trifunctional amino acids of formula I wherein each $R_2$ is lysine. $R_3$ is 0 backbone atoms. The resulting synthetic growth modulator analog is of the following specific structure:

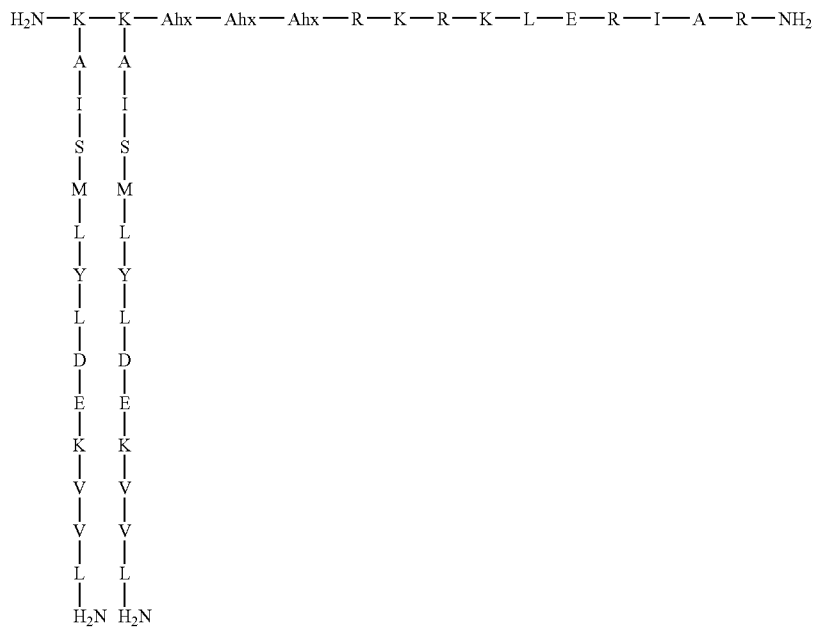

and is sometimes referred to as B2A2. In the foregoing structure, "Ahx" is 6-amino hexanoic acid, sometimes also called "6-Ahx" or "Hex". The single letters are standard amino acid single letter abbreviations for the naturally coded amino acids. The two chains of SEQ ID NO:7 link to lysine of the $R_2$ position via a peptide bond with the epsilon amines of the lysine side chains.

EXAMPLE 3

The compound of Example 2 (B2A2) was tested in cell osteogenic differentiation studies to determine the analog's ability to stimulate osteogenic activity. B2A2 binds to BMP receptors, and that receptor activation is associated with the expression of the osteogenic transcription factor Smad and repression of MAPK followed by a phenotypic transformation in which ALP is induced. Referring now to FIG. 1A, the induction of osteogenic differentiation in C3H10T½ cells by BMP-2 in the presence and absence of B2A2 is illustrated. Treatment of C3H10T½ cells with B2A2 alone (up to 10 μg/mL) only slightly increases alkaline phosphatase (ALP) activity. However, B2A2 plus BMP-2 at suboptimal concentrations (100 ng/mL) results in significant increases of ALP activity. The $EC_{50}$ for BMP-2 is typically 300 ng/mL.

C3H10T½ cells were seeded onto 96-well plates, treated with BMP-2 alone or in combination with B2A2 at different concentrations (solid circles represent BMP-2 at 100 ng/mL, solid squares represent BMP-2 at 50 ng/mL and unshaded squares represent samples with no BMP-2). The cells were incubated for 5 days, and then assayed for ALP activity. ALP activity was assayed by conversion of para-nitrophenol phosphate (PNPP).

B2A2 alone had little if any effect on ALP activity in the dose range between about 0.075-10.0 μg/mL as illustrated in FIG. 1A. The induction of ALP activity was enhanced when cells are treated with 100 ng/mL of BMP-2 together with B2A2. Co-treatment was not additive, but was synergistic. Thus B2A2 is a partial agonist of BMP-2.

Figure 1B:
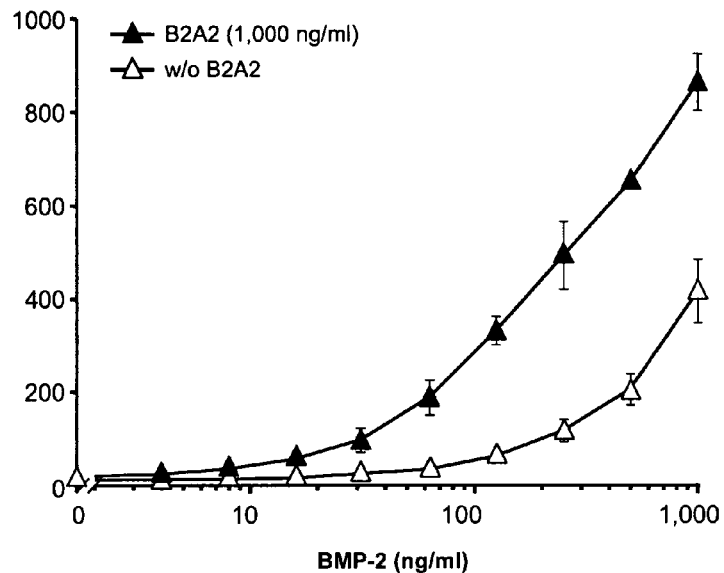

Referring now to FIG. 1B, the synergistic effect of B2A2 and BMP-2 is illustrated under conditions where the B2A2 concentration is constant at about 1000 ng/mL while the concentration of BMP-2 is varied. Using a fixed concentration of B2A2 (1 μg/mL), augmentation of ALP activity was seen from as low as 25 ng BMP-2/mL to as high as 1000 ng BMP-2/mL. The threshold for BMP-2 induction of ALP starts at ~30 ng/mL but in the presence of 1000 ng/mL B2A2 the threshold was lowered to about 3 ng/mL BMP-2.

EXAMPLE 4

Figure 2:
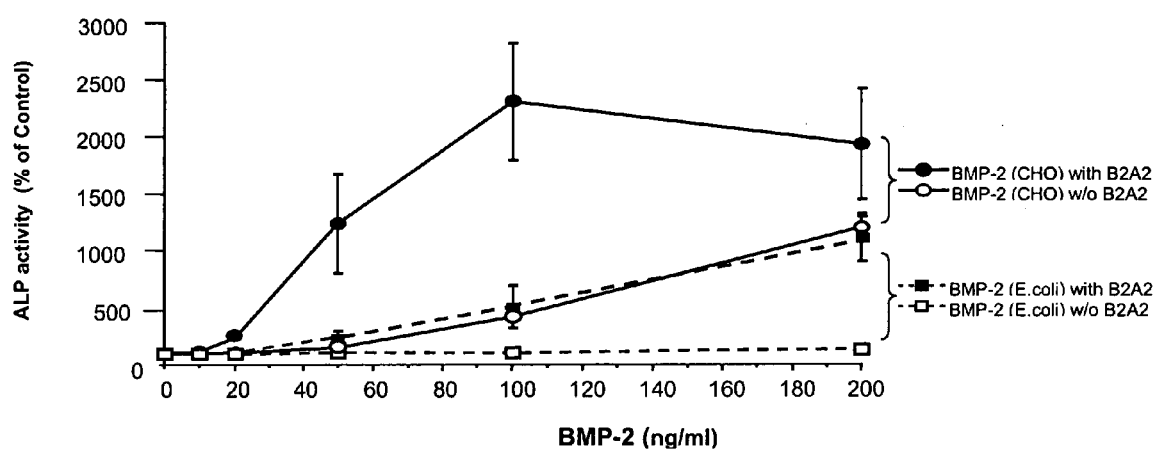
FIG. 2 is a graph illustrating that B2A2 enhances the activity of recombinant human BMP-2 obtained from CHO cell and E.coli commercial production methods.

B2A2 was tested to determine whether B2A2 enhanced the biological effects of CHO-produced rhBMP-2. Referring now to FIG. 2, induction of ALP activity in C2C12 cells by recombinant BMP-2 protein (rh-BMP-2) and B2A2 is illustrated. Rh-BMP-2 is commercially available from either *E. coli* or mammalian CHO cell production methods with slightly different potencies, yet B2A2 augments both types of rhBMP-2. Mouse C2C12 cells were seeded onto 96 well plates, treated with B2A2 in combination with human BMP-2 derived from different sources (●/○ CHO versus ■/□ *E. coli*), incubated for 4 days, and then assayed for ALP activity as described. B2A2 was applied at 1000 ng/mL, and BMP-2 at the concentrations indicated in the graph. B2A2 increased the efficacy of *E. coli*-derived BMP-2 to levels similar to that of CHO cell-derived BMP-2, and the efficacy of CHO-derived BMP-2 is further increased by B2A2. Points represent means of quintuplicate determinations±SD.

EXAMPLE 5

Figure 3:
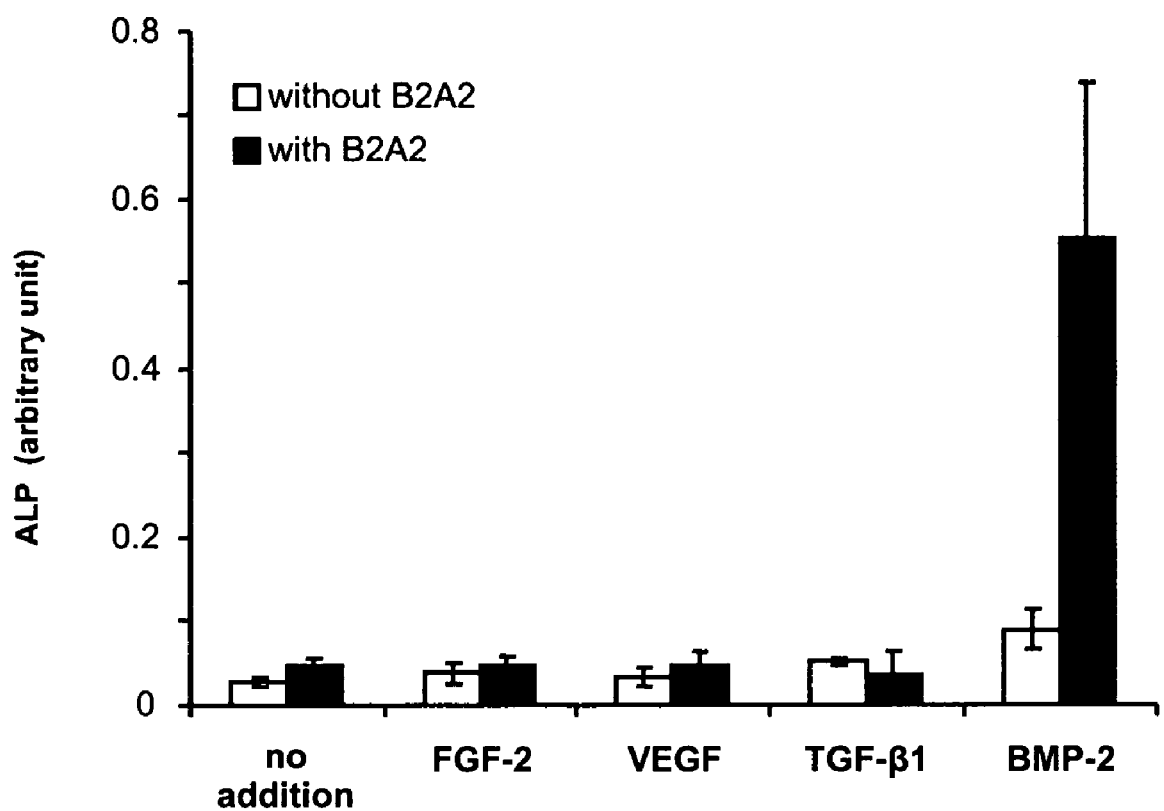
FIG. 3 is a graph illustrating that the synergistic effect of B2A2 was specific to BMP-2.

B2A2 was tested in combination with other growth factors including FGF-2, VEGF, and tGF-β1 for induction of ALP in C2C12 cells. Referring now to FIG. 3, induction of ALP activity by BMP-2 but not various other growth factors in the presence of B2A2 is illustrated. Treatments of FGF-2, TGF-B, VEGF alone failed to induce ALP in C2C12 cells in the presence of B2A2 demonstrating that BMP-2 is the effector in the combination of B2A2 and BMP-2. Mouse C2C12 cells were cultured as described for FIG. 1A, treated with a combination of various growth factors plus or minus B2A2, incubated for 3 days, and then assayed for ALP activity as described for FIG. 1A. FGF-2 was used at 50 ng/mL, VEGF at 25 ng/mL, TGF-β1 at 50 pg/mL, BMP-2 at 50 ng/mL, and B2A2 at 1000 ng/mL. Bars represent means of quintuplicate determinations±SD.

EXAMPLE 6

Figure 4:
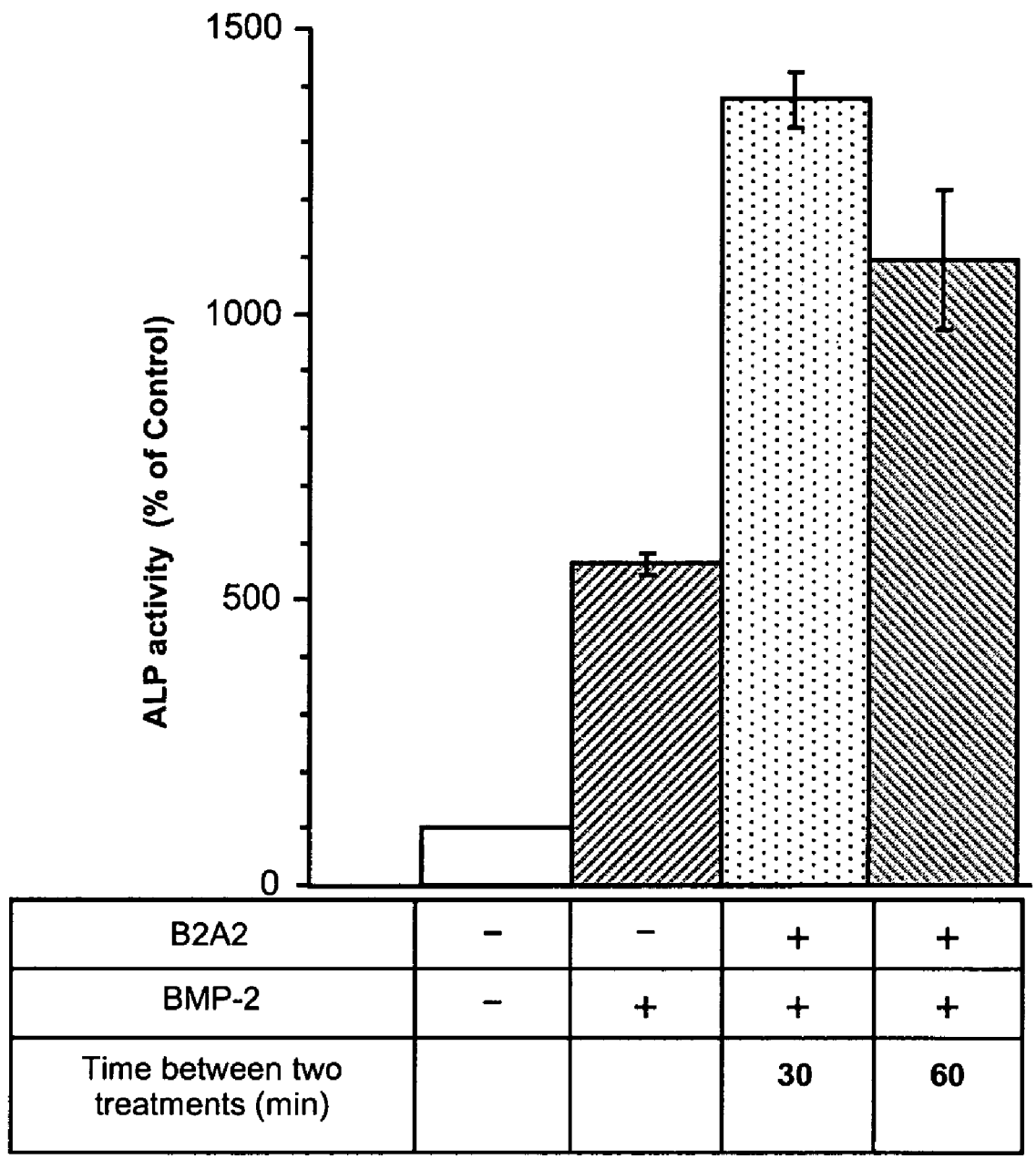
FIG. 4 is a graph illustrating the induction of ALP activity despite the temporal separation of the addition of B2A2 and BMP-2 to the C2C12 cell line.

B2A2 was tested to determine whether temporal dissociation of B2A2+BMP-2 administered to cells affected the BMP-2 induction of osteogenic activity by the cell. Referring now to FIG. 4, the induction of ALP activity is illustrated despite the temporal separation of the addition of B2A2 and BMP-2 to the C2C12 cell line. Co-administration of the agents is not required since serial addition of B2A2 followed by washout and addition of BMP-2 in intervals up to one hour was effective in inducing ALP activity. Mouse C2C12 cells were cultured as before and B2A2 (1000 ng/mL) was added to some wells. After a 45 minute incubation all wells were rinsed with fresh medium and the medium was replaced. To one set of wells, BMP-2 (200 ng/mL) was added, another set was incubated an additional 30 min and then BMP-2 added, and finally yet another set was incubated an additional 60 minutes and then BMP-2 added. After 5 days ALP activity was measured. The synergistic effect was still observed despite the temporal separation of B2A2 and BMP-2 administration and the washout in between. Data is the means of triplicates±SD.

EXAMPLE 7

Figure 5:
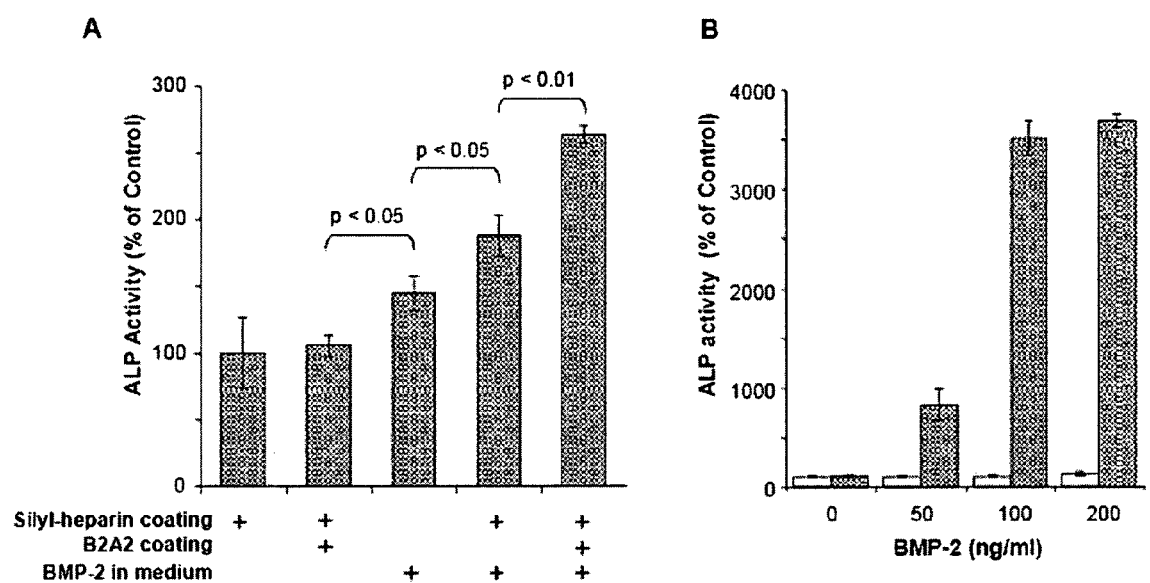
FIG. 5 is a graph illustrating that B2A2-coated surfaces enhanced BMP-2 activity. Surfaces of a variety of compositions were first coated with silyl heparin under sterile conditions in tissue culture dishes (a 1% solution in acid ethanol incubated 30 min at 37° C., rinsed with $H_2O$, dried at 56° C.).

B2A2 was tested to determine whether spatial dissociation of B2A2 plus BMP-2 administered to cells affected the BMP-2 induction of osteogenic activity in the cells. Referring now to FIG. 5, the induction of ALP activity is illustrated despite the spatial separation of the addition of B2A2 and BMP-2. In FIG. 5A, a polystyrene surface of 96-well plates were first coated by silyl-heparin (open bars), followed by a 1 μg/mL solution of B2A2 (solid bars) in PBS for (1 hr at 37° C.) and rinsed in PBS and dried at room temperature. C2C12 cells were subsequently seeded at densities that resulted in confluent monolayers, and after allowance for attachment (1-2 hrs), BMP-2 at 50 ng/mL was added to the cultures. ALP activity was measured five days later. Data is the means of triplicates±SD. While silyl-heparin alone potentiates BMP-2 activity, the ALP activity induced by B2A2 and BMP-2 together is more profound.

In FIG. 5B, stainless steel wafers were first coated with silyl-heparin (open bars) followed by 100 μg/mL B2A2 in PBS as a second coating (solid bars) and rinsed in PBS and dried at room temperature. Wafers were coated separately in wells of a 24-well plate and transferred to a fresh untreated plate prior to cell seeding.

C2C12 cells were subsequently seeded at densities that resulted in confluent monolayers, and after allowance for attachment (1-2 hrs), BMP-2 at the concentrations indicated in the graph were added to the cultures. ALP activity was measured five days later. Data is the means of triplicates±SD. The results indicate that the enhancement of BMP-2 by B2A2 on stainless steel was profound. Similar results were observed for silyl-heparin+B2A2 coating on titanium wafers in the presence of BMP-2.

EXAMPLE 8

Figure 6:
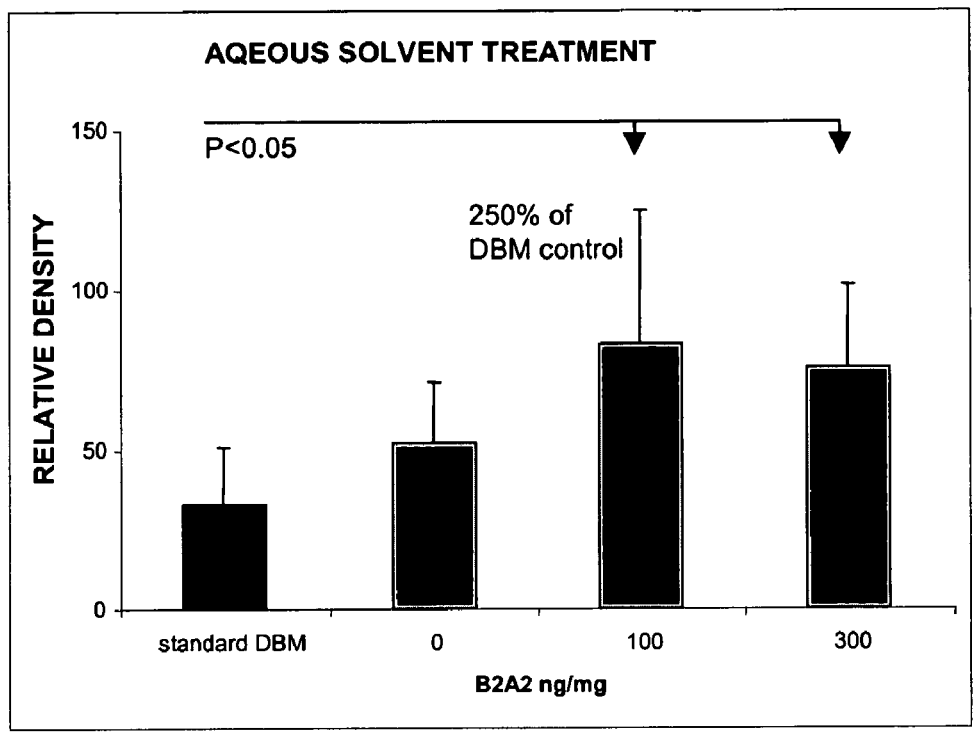
FIG. 6 is a graph illustrating the relative density from radiographic image analysis from athymic rats implanted at 3 weeks.

B2A2 was tested to determine if B2A2 could augment demineralized bone matrix material (DBM) in an ectopic model of bone formation. Referring now to FIG. 6, the synergistic activity of B2A2 with DBM for bone formation is illustrated. B2A2 was coated onto DBM. B2A2 (100 ng/mg or 300 mg/mL) in a small volume of water (pH 4) was added to DBM (100 μL/g), mixed, and air-dried at 37° C. The resultant DBM was then further dried overnight in a vacuum oven.

The B2A2-coated DBM was implanted into the muscle of athymic rats and the radiographic density of the implant area is examined after 3 weeks. There was a 250% increase in relative bone density after 3 weeks in comparison to DBM without B2A2 and a 650% increase in bone density after 6 weeks in comparison to DBM without B2A2 (data not shown), As indicated in FIG. 6, there was a statistically significant increase in radiographic density in B2A2 coated-DBM muscle at both time points.

B2A2 can be employed as an additive to demineralized bone matrix (DBM) and bone graft materials to maximize the bioactivity of BMP-2. B2A2 augments the bioactivity of BMP-2 found in DBM (exogenous) and in bone undergoing repair (endogenous). The clinical use of B2A2 provides a new and novel treatment strategy applicable to accelerating bone repair.

Table 2 below summarizes the biochemical interactions of B2A2, and the modulation of alkaline phosphatase, wherein modulation was monitored using C2C12 cells.

TABLE 2

| Biochemical interactions of B2A2 | |
|---|---|
| Interaction with heparin | Yes |
| MAP kinase phosphorylation | Yes |
| Positive modulation of alkaline phosphatase | |
| BMP-2 (*E. coli*) | Yes |
| BMP-2 (Chinese hamster ovary cells) | Yes |
| BMP-7 (mammalian cell) | No |
| Modulation via a coating of alkaline phosphatase | |
| B2A2 coating, BMP-2 in solution | Yes |
| BMP-2 coating, B2A2 in solution | Yes |
| Silyl-heparin/BMP-2 coating, B2A2 in solution | Yes |

EXAMPLE 9

A compound of the present invention was synthesized by solid phase peptide chemistry with the general structure of formula II wherein X is a BMP-2 receptor binding amino acid sequence having the sequence AISMLYLDEKVVL (SEQ ID NO:7) wherein SEQ ID NO:7 was stepwise synthesized in parallel from the $R_5$ trifunctional amino acid of formula II when $R_6$ is 0 backbone atoms and $R_5$ is lysine. The resulting synthetic growth modulator analog is of the following specific structure:

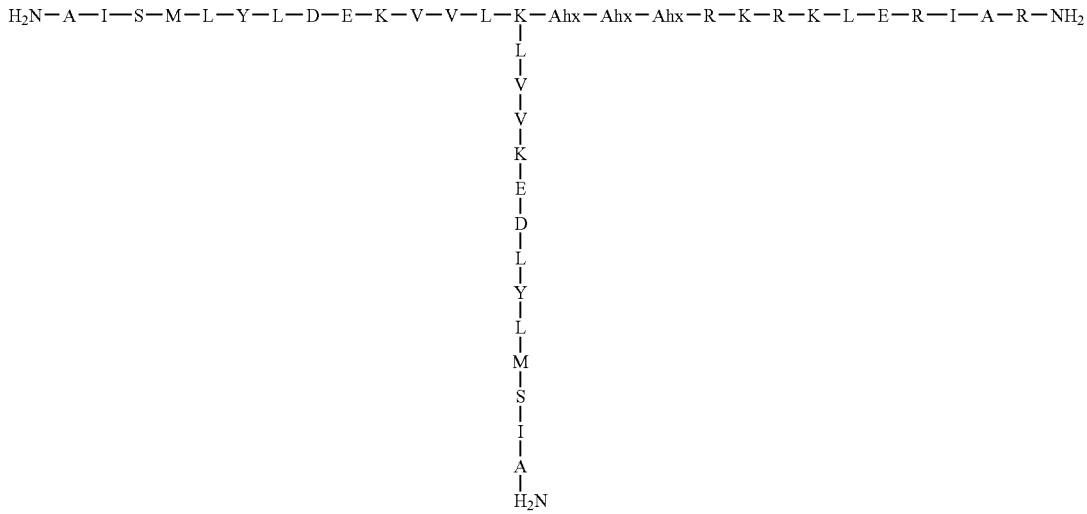

and is sometimes called B2A2-K-NS. In the foregoing structure, "Ahx" is 6-amino hexanoic acid, sometimes also called "6-Ahx" or "Hex". The single letters are standard amino acid single letter abbreviations for the naturally coded amino acids. The chain of SEQ ID NO:7 is grown from the alpha and epsilon amine groups of the lysine in the $R_5$ position. The theoretical molecular weight of B2A2-K-NS is 5486.9.

EXAMPLE 10

Figure 7:
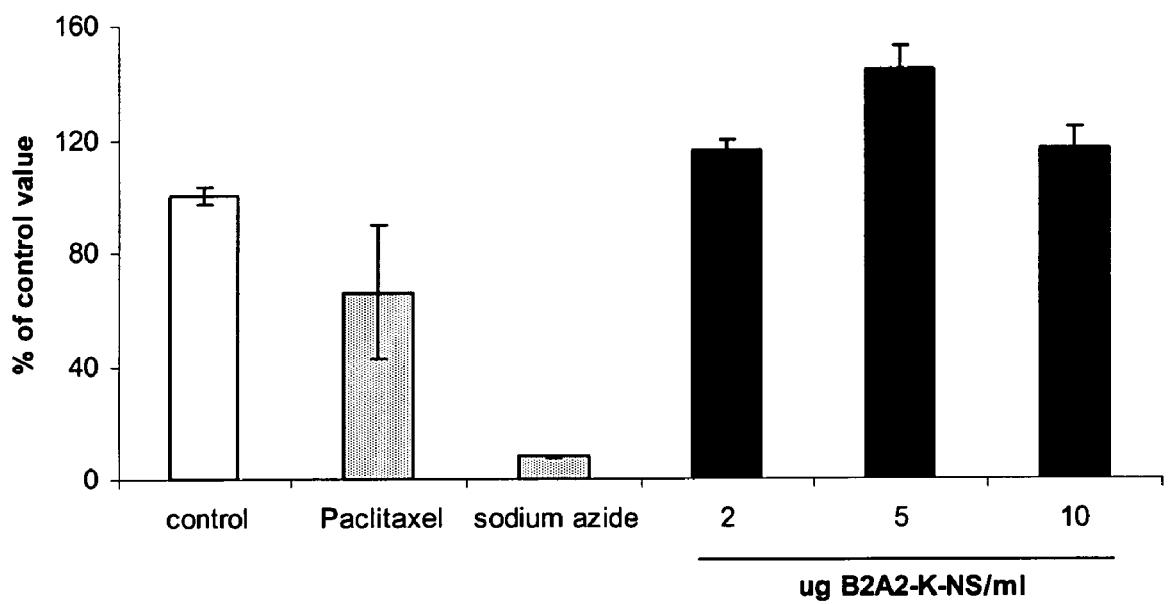
FIG. 7 is a graph illustrating the relative number of L6 cells in culture after treatment with cytotoxic agents or B2A2-K-NS.

The synthetic growth factor analog of Example 9 (B2A2-K-NS) was tested for deleterious effect on L6 cells. Referring now to FIG. 7, the relative number of L6 cells in culture after treatment with cytotoxic agents or B2A2-K-NS is illustrated. L6 cells were treated with 100 ng/mL of Paclitaxel or 0.01% sodium azide and the effects of these cytotoxic agents were compared to L6 cells treated with varying concentrations of B2A2-K-NS after three days of treatment. B2A2-K-NS induced cell proliferation above control values at concentrations between 2-10 μg/mL. Similar results were observed in human fetal osteoblasts, C3H10T½ cells and MC-3T3-E1 cells.

EXAMPLE 11

Figure 8:
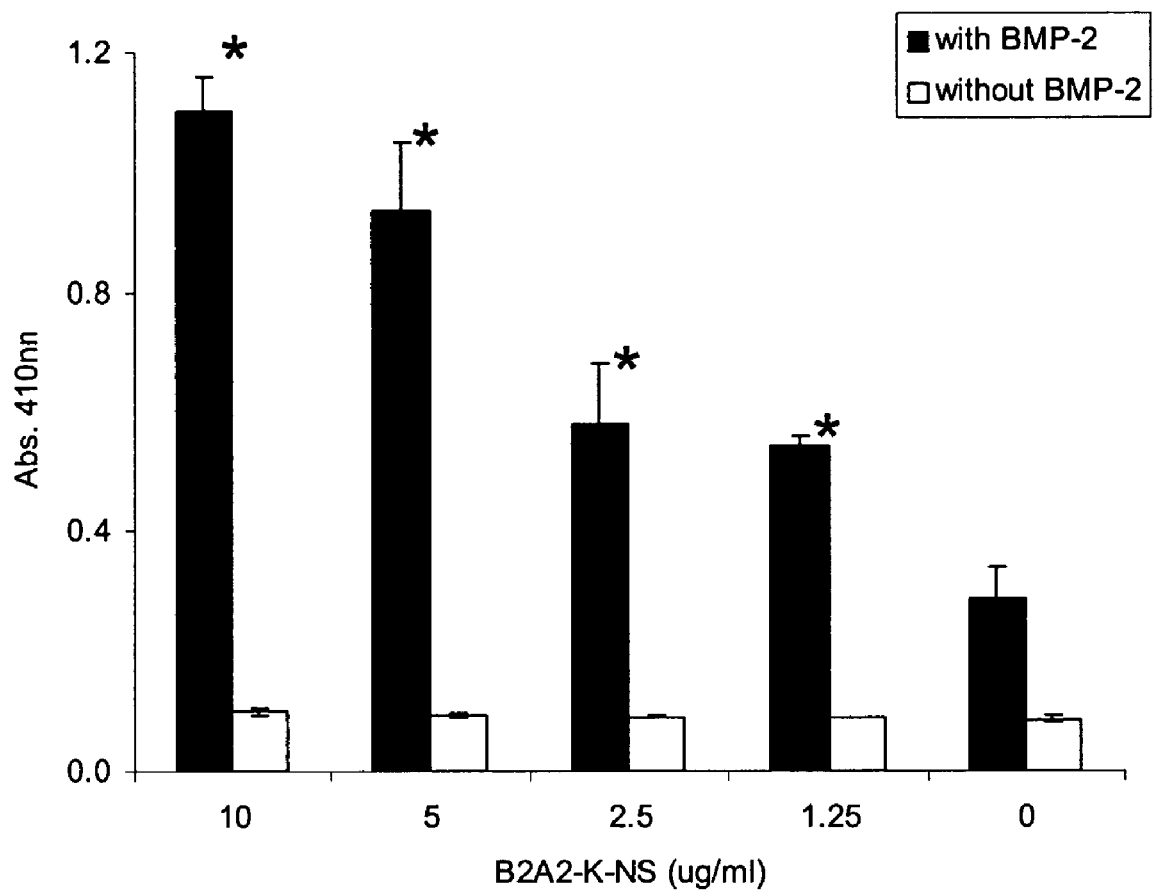
FIG. 8 is a graph illustrating the induction of osteogenic differentiation in C2C12 cells with varying concentrations of B2A2-K-NS in the presence and absence of BMP-2.

B2A2-K-NS was tested in cell osteogenic differentiation studies to determine the ability of the synthetic growth analog to stimulate osteogenic activity. Referring now to FIG. 8, the induction of osteogenic differentiation in C2C12 cells with varying concentrations of B2A2-K-NS in the presence and absence of BMP-2 is illustrated. Treatment of C2C12 cells with B2A2-K-NS alone (up to 10 μg/mL) only slightly increases alkaline phosphatase (ALP) activity, however, B2A2-K-NS plus BMP-2 results in significant increases of ALP activity even at normally sub-threshold concentrations of BMP-2. C2C12 cells were seeded onto 96-well plates, treated with varying concentrations of B2A2-K-NS in the presence (solid bars) and absence (open bars) of BMP-2 at 100 ng/mL. The cells were incubated for 4 days, and then assayed for ALP activity. ALP activity was assayed by conversion of para-nitrophenol phosphate (PNPP). B2A2-K-NS had no effect on the induction of ALP activity at concentrations up to about 10 μg/mL. B2A2-K-NS substantially augments ALP activity induced by suboptimal amounts of BMP-2 (100 ng/mL). Similar results were obtaining with C3H10T½ cells.

EXAMPLE 12

B2A2-K-NS was tested for its ability to induce cells of preosteoblast origin to migrate to a stimulated wound margin. Murine C3H10T½, MC3T3 cells or hFOB were grown to near confluency in vitro. A stimulated wound was made by scraping the cells away from the substrate. The cells were allowed to migrate for 6 hours after which migration was monitored via microscopy. Statistical significance was determined using ANOVA followed by post hoc testing using multiple comparison versus control group (Dunnett's Method). FGF-2 was used as a positive control reference material and induced a significant increase in migrating cells compared to controls (data not shown). Table 3 summarizes the increase in migrating cells at the simulated wound margin induced by about 0.2 to 2.0 μg/mL B2A2-K-NS.

TABLE 3

| μg B2A2-K-NS/mL | Mean | Std Dev | % of control |
|---|---|---|---|
| Migrating C3H10T1/2 cells/field | | | |
| 0.0 | 104.7 | 18.1 | 100 |
| 0.2 | 148.4 | 21.5 | 142 |
| 0.5 | 177.3 | 24.3 | 169 |
| 1.0 | 214.6 | 34.9 | 205 |
| 2.0 | 197.4 | 12.5 | 188 |
| Migrating MC-3T3 cells/field | | | |
| 0.0 | 162.8 | 43.3 | 100 |
| 0.2 | 251.2 | 37.2 | 154 |
| 0.5 | 286.7 | 24.0 | 176 |
| 1.0 | 297.7 | 34.3 | 183 |
| 2.0 | 254.3 | 41.4 | 156 |
| Migrating hFOB cells/field | | | |
| 0.0 | 92.4 | 33.5 | 100 |
| 0.2 | 149.7 | 25.3 | 162 |
| 0.5 | 164.7 | 28.1 | 178 |
| 1.0 | 192.4 | 33.2 | 208 |
| 2.0 | 165.9 | 27.6 | 179 |

EXAMPLE 13

Figure 9:
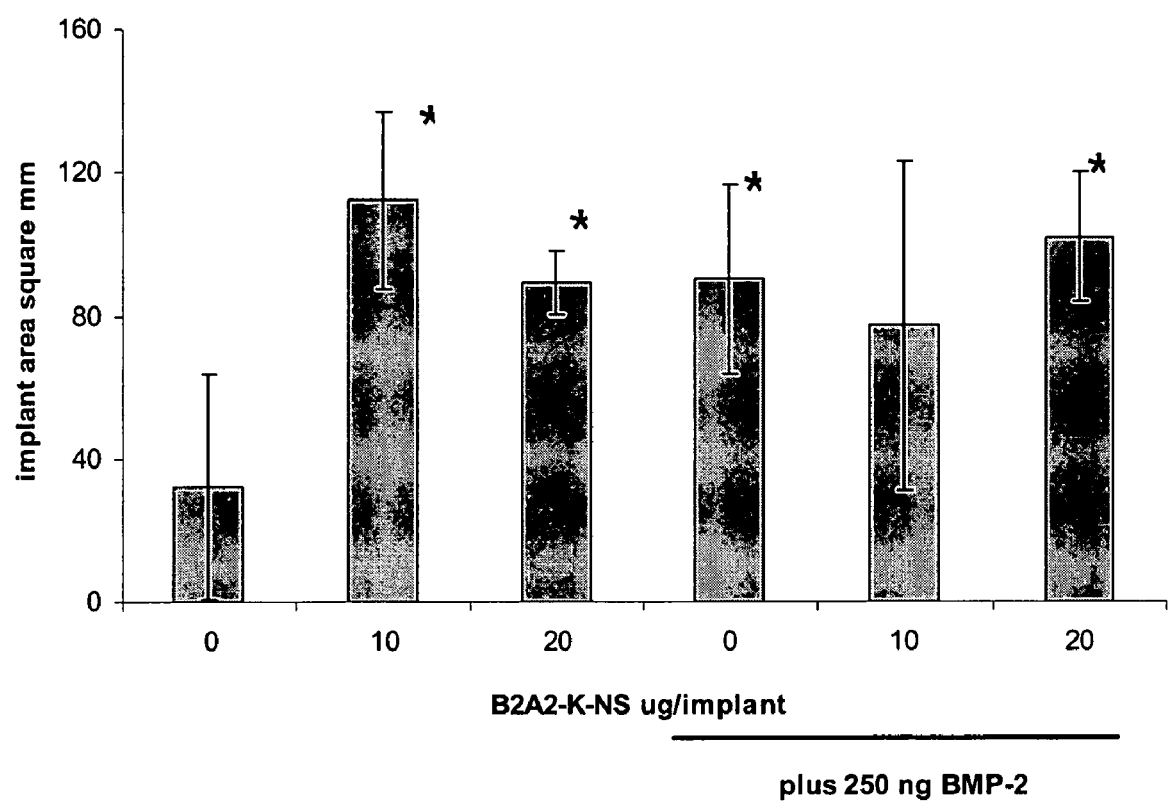
FIG. 9 is a graph comparing the area of explants excised from an area implanted with matrigel containing B2A2-K-NK analog with and without BMP-2.

B2A2-K-NS analog was tested for its effect in vivo. Referring now to FIG. 9, a comparison of the area of explants excised from an area implanted with Matrigel™ containing B2A2-K-NK analog with and without BMP-2 is illustrated. Adult rats were implanted with Matrigel™ with and without BMP-2 and B2A2-K-NS and after 14 days the residual gel was surgically removed and measured. Nearly all of the implant sites that received B2A2-K-NS, BMP-2, and BMP-2 and B2A2-K-NS had palpable sites upon inspection whereas the control implant with carrier only had been largely adsorbed. Further, the explants from sites that had received B2A2-K-NS, BMP-2 or a combination of B2A2-K-NS plus BMP-2 had significantly larger explants. The morphology of the explants differed with differing explant compositions. Animals receiving only carrier had residual plugs that were small and tended to have morphology with poor cellular organization. Animals receiving B2A2-K-NS had plugs with morphologies consistent with fibrocartilage. Animals receiving BMP-2 treatments developed plugs containing increased numbers of cells accompanied by a moderate amount of organization that was consistent with developing membranous ossification. In animals receiving B2A2-K-NS plus BMP-2, an increase in cell density was observed along with an organization consistent with developing membranous ossification. The cell density was greater than observed for controls or B2A2-K-NS but less than the cell density observed for explants from animals receiving BMP-2 alone (data not shown).

EXAMPLE 14

Figure 10:
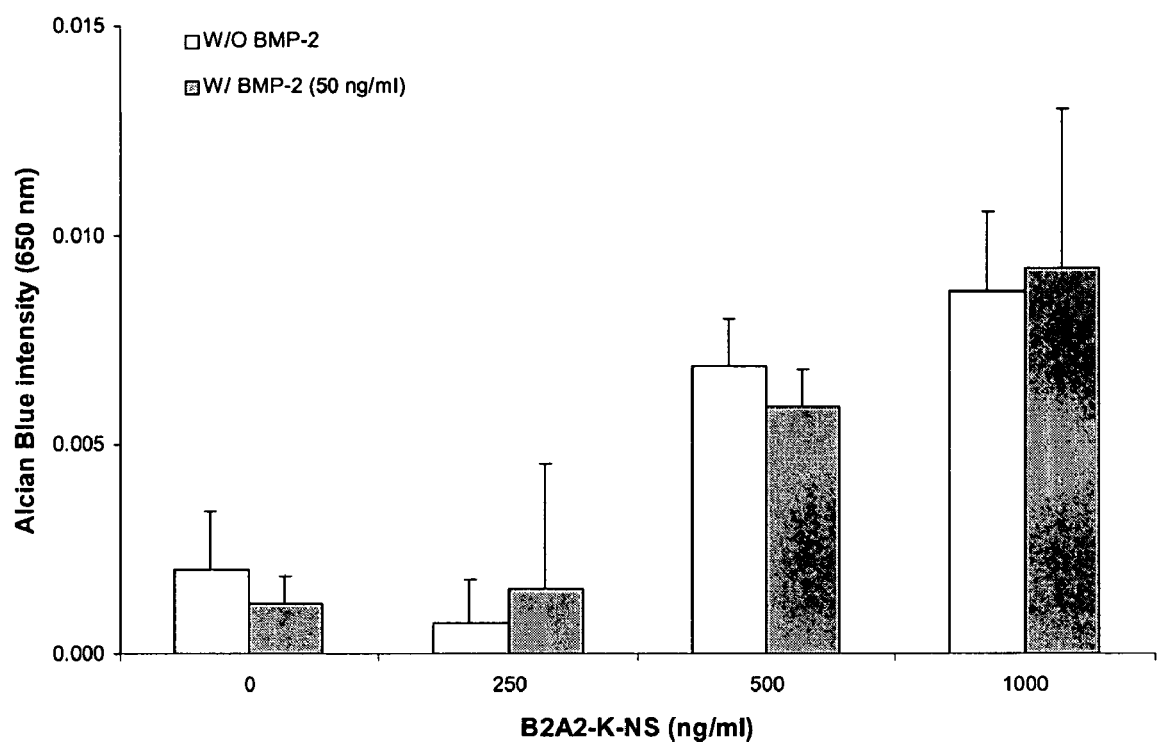
FIG. 10 is a graph illustrating Alcian staining of chondrogenic pathway proteins in C3H10T½ cells whose expression was stimulated by B2A2-K-NS treatment.

The B2A2-K-NS analog was tested in cell osteogenic differentiation studies to determine the synthetic growth analogs ability to stimulate osteogenic activity. Referring now to FIG. 10, the induction of osteogenic differentiation in C2C12 cells by B2A2-K-NS in the presence and absence of suboptimal concentrations (100 ng/mL) of BMP-2 is illustrated. Treatment of C2C12 cells with B2A2-K-NS alone (up to 10 μg/mL) only slightly increases alkaline phosphatase (ALP) activity. However, B2A2-K-NS plus BMP-2 results in significant increases of ALP activity even at normally sub-threshold concentrations of BMP-2. C2C12 cells were seeded onto 96-well plates, treated with B2A2-K-NS at different concentrations in the presence (solid bars) or absence (unshaded bars) of 100 ng/mL BMP-2. The cells were incubated for 4 days, and then assayed for ALP activity. ALP activity was assayed by conversion of para-nitrophenol phosphate (PNPP).

EXAMPLE 15

The B2A2-K-NS analog was tested for its ability to induce phenotypic expression changes in cells independent of BMP-2 (data not shown). MC3T3 cells were stimulated with B2A2-K-NS and changes in the expression of osteocalcin, osteoponin, and type II collagen were observed as measured with specific antibodies to each which were subsequently detected with secondary antibodies conjugated to HPRO. The developed membranes were digitized with a scanner and converted to gray scale with color inversion with software.

Referring now to FIG. 10, Alcian staining of C3H10T½ cells for chondrogenic pathway derived proteins is illustrated. B2A2-K-NS increases the amount of Alcian blue stainable material produced in C3H10T½ cells at 10 days after stimulation. Suboptimal amounts of BMP-2 (50 ng/mL) did not augment the increase in Alcian blue stainable material.

EXAMPLE 16

A compound of the present invention was synthesized by solid phase peptide chemistry with the general structure of formula II wherein X is a BMP receptor binding amino acid sequence having the sequence LYFDESSNVILKK (SEQ ID NO:9) wherein SEQ ID NO:9 was stepwise synthesized in parallel from the $R_5$ trifunctional amino acid of formula II when $R_6$ is 0 atoms and $R_5$ is a lysine. In synthesis, side chains of lysine residues other than the $R_5$ lysine were protected, as were other reactive side chains, with selective deprotection following synthesis. The resulting synthetic growth modulator analog is of the following specific structure:

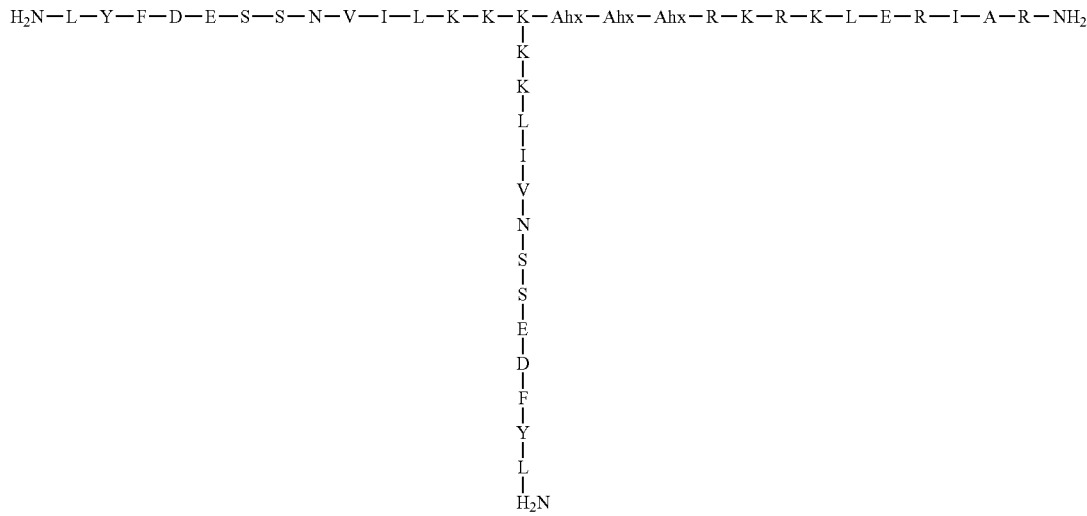

and is sometimes called B7A1-K-NS. In the foregoing structure, "Ahx" is 6-amino hexanoic acid, sometimes also called "6-Ahx" or "Hex". The single letters are standard amino acid single letter abbreviations for the naturally coded amino acids. The chain of SEQ ID NO:9 is grown from the alpha and epsilon amine groups of the lysine in the $R_5$ position.

EXAMPLE 17

Figure 11:
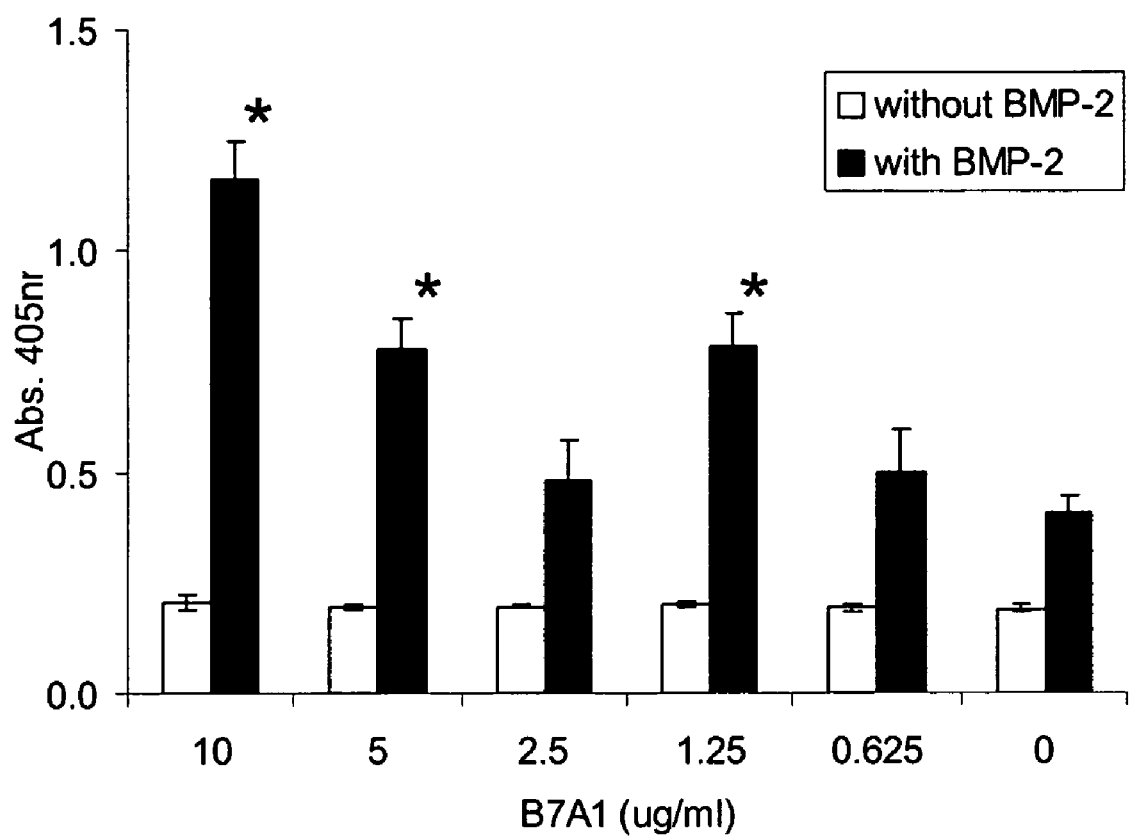
FIG. 11 is a graph illustrating the induction of osteogenic differentiation in C2C12 cells by B2A7-K-NS in the presence and absence of suboptimal concentration of BMP-2.

B7A1-K-NS was tested in cell osteogenic differentiation studies to determine the ability of the synthetic growth analog to stimulate osteogenic activity. Referring now to FIG. 11, the induction of osteogenic differentiation in C2C12 cells with varying concentrations of B7A1-K-NS in the presence and absence of BMP-2 is illustrated. Treatment of C2C12 cells with B2A2 alone (up to 10 μg/mL) did not affect the production of ALP activity. However, B7A1-K-NS plus BMP-2 results in significant increases of ALP activity even at normally sub-threshold concentrations (100 ng/mL) of BMP-2. C2C12 cells were seeded onto 96-well plates, treated with varying concentrations of B2A2 in the presence (solid bars) and absence (open bars) of BMP-2 at 100 ng/mL. The cells were incubated for 4 days, and then assayed for ALP activity. ALP activity was assayed by conversion of para-nitrophenol phosphate (PNPP). B7A1-K-NS had no effect on the induction of ALP activity at concentrations up to about 10 μg/mL. B7A1-K-NS substantially augments ALP activity induced by suboptimal amounts of BMP-2 (100 ng/mL). Similar results were obtaining with C3H10T½ cells.

EXAMPLE 18

A compound of the present invention is synthesized by solid phase peptide chemistry with the general structure of formula I wherein X is a BMP-2 receptor binding amino acid sequence having the sequence ISMLYLDENEKVVLKNY (SEQ ID NO:8) wherein SEQ ID NO:8 is stepwise synthesized in parallel from $R_2$ trifunctional amino acids of formula I and wherein each $R_2$ is lysine. The resulting synthetic growth modulator analog is of the following specific structure:

In the foregoing structure, "Ahx" is 6-amino hexanoic acid, sometimes also called "6-Ahx" or "Hex". The single letters are standard amino acid single letter abbreviations for the naturally coded amino acids. The two chains of SEQ ID NO:8 link to lysines in the $R_2$ position via a peptide bond with the secondary amine of the lysine side chains.

EXAMPLE 19

A compound of the present invention is synthesized by solid phase peptide chemistry with the general structure of formula I wherein X is a BMP receptor binding amino acid sequence having the sequence LYVDFSDVGWNDW (SEQ ID NO:10) wherein SEQ ID NO:10 is stepwise synthesized in parallel from the $R_2$ trifunctional amino acids of formula I and wherein each $R_2$ is lysine. The resulting synthetic growth modulator analog is of the following specific structure:

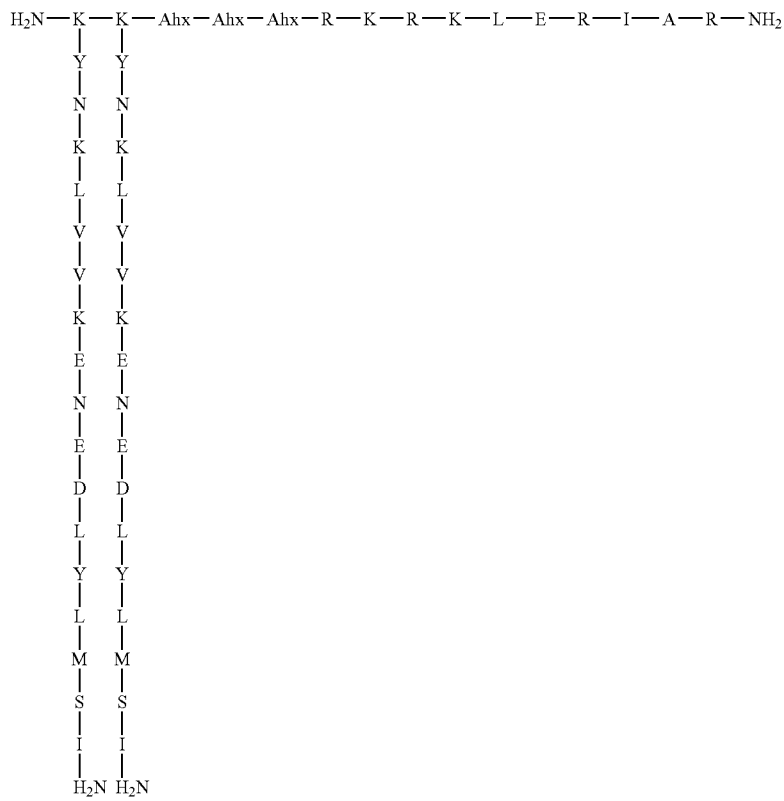

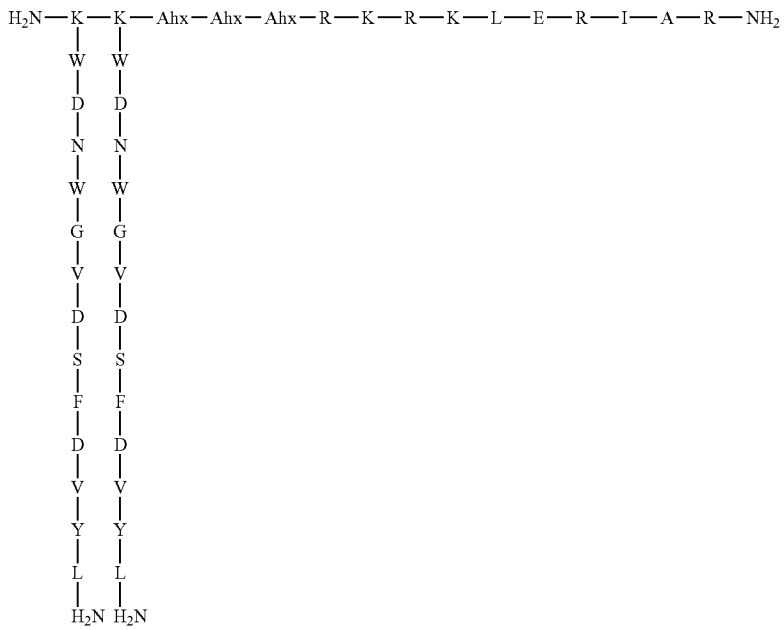

In the foregoing structure, "Ahx" is 6-amino hexanoic acid, sometimes also called "6-Ahx" or "Hex". The single letters are standard amino acid single letter abbreviations for the naturally coded amino acids. The two chains of SEQ ID NO:10 link to lysines in the $R_2$ position via a peptide bond with the secondary amines of the lysine side chains.

EXAMPLE 20

A synthetic growth modulator analog of the BMP family is synthesized by solid phase peptide chemistry with the general structure of formula I wherein X is a BMP receptor binding amino acid sequence having the sequence CAISM-LYLDENEKVVL (SEQ ID NO:12) wherein SEQ ID NO:12 is stepwise synthesized in parallel from $R_2$ trifunctional amino acids of formula I and where $R_2$ are each lysine. The resulting synthetic growth modulator analog is of the following specific structure:

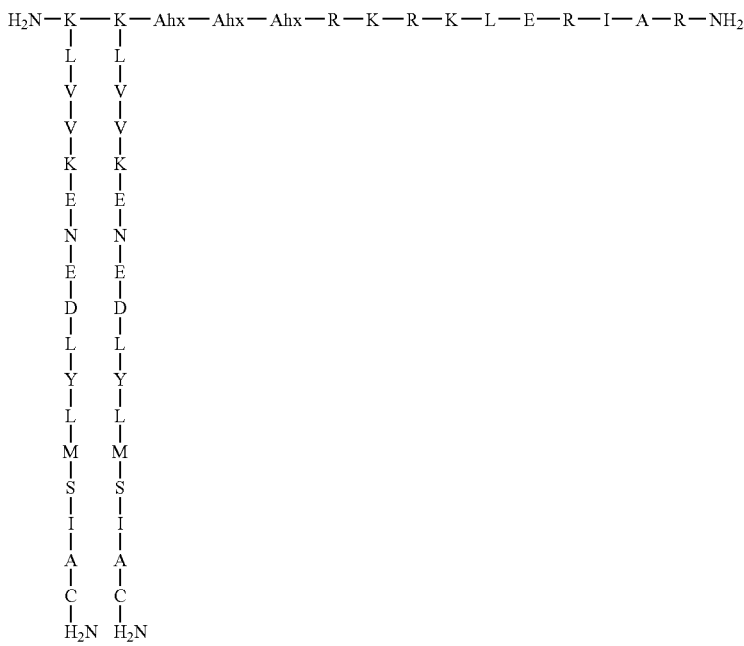

In the foregoing structure, "Ahx" is 6-amino hexanoic acid, sometimes also called "6-Ahx" or "Hex". The single letters are standard amino acid single letter abbreviations for the naturally coded amino acids. The two chains of SEQ ID NO:12 link to lysines in the $R_2$ position via a peptide bond with the secondary amines of the lysine side chains.

EXAMPLE 21

A compound of the present invention is synthesized by solid phase peptide chemistry with the general structure of formula I wherein X is a BMP receptor binding amino acid sequence having the sequence AFYCHGECPFPLADHL (SEQ ID NO:13) wherein SEQ ID NO:13 is stepwise synthesized in parallel from $R_2$ trifunctional amino acids of formula I and wherein each $R_2$ is lysine. The resulting synthetic growth modulator analog is of the following specific structure:

In the foregoing structure, "Ahx" is 6-amino hexanoic acid, sometimes also called "6-Ahx" or "Hex". The single letters are standard amino acid single letter abbreviations for the naturally coded amino acids. The two chains of SEQ ID NO:13 link to lysines in the $R_2$ position via a peptide bond with the epsilon amines of the lysine side chains.

EXAMPLE 22

A compound of the present invention is synthesized by solid phase peptide chemistry with the general structure of formula I wherein X is a BMP receptor binding amino acid sequence having the sequence PFPLADHLNST-NHAIVQTLVNSV (SEQ ID NO:14) wherein SEQ ID NO:14 is stepwise synthesized in parallel from $R_2$ trifunctional amino acids of formula I and wherein each $R_2$ is a lysine. The resulting synthetic growth modulator analog is of the following specific structure:

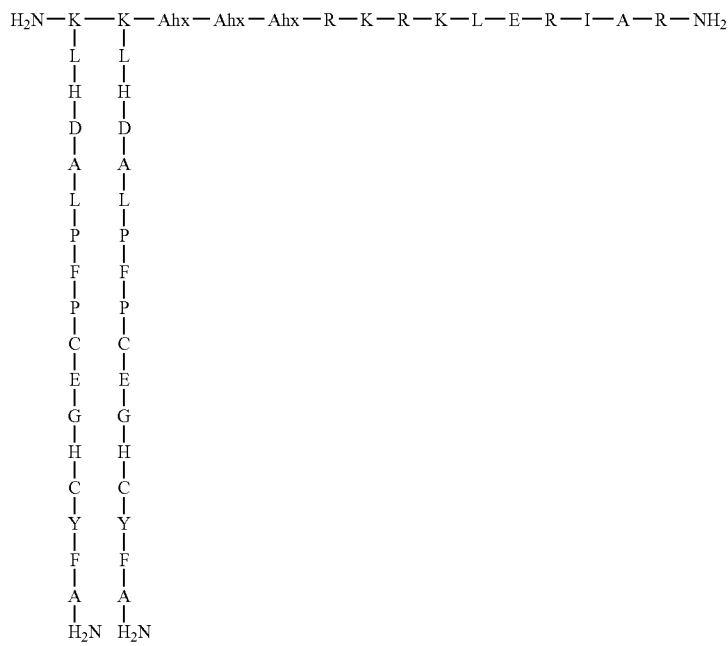

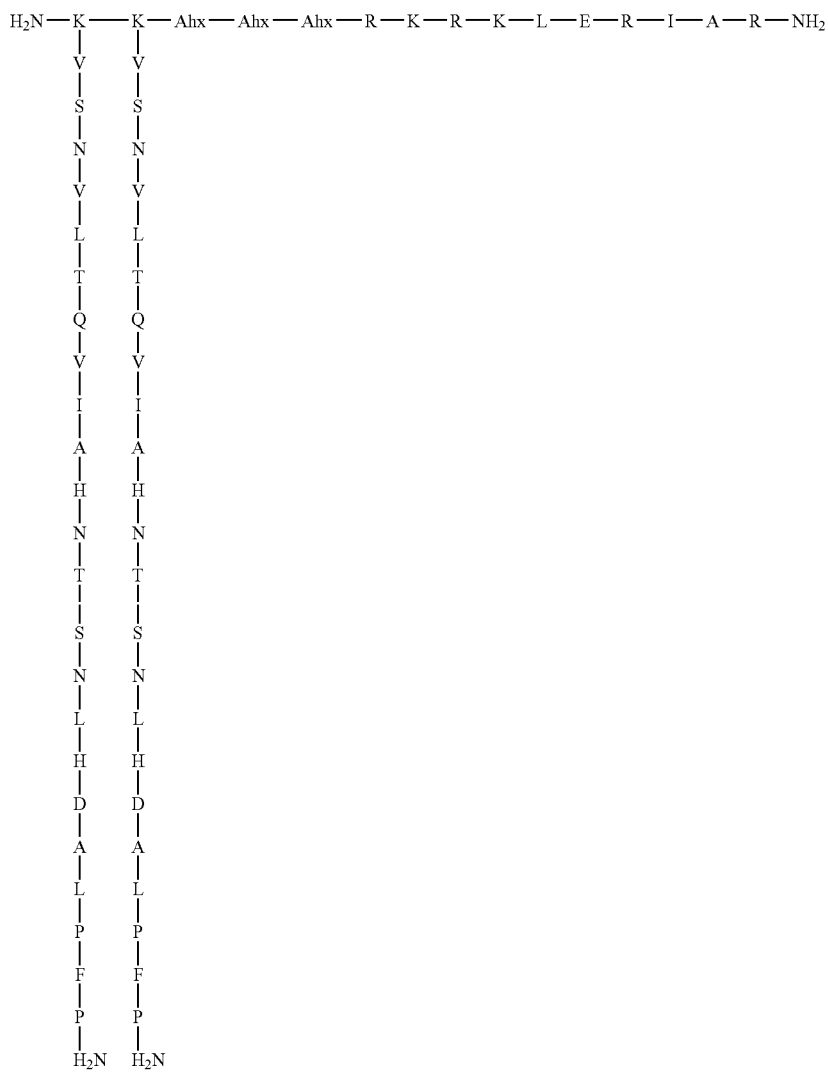

In the foregoing structure, "Ahx" is 6-amino hexanoic acid, sometimes also called "6-Ahx" or "Hex". The single letters are standard amino acid single letter abbreviations for the naturally coded amino acids. The two chains of SEQ ID NO:14 link to lysines in the $R_2$ position via a peptide bond with the secondary amines of the lysine side chains.

EXAMPLE 23

A compound of the present invention was synthesized by solid phase peptide chemistry with the general structure of formula I wherein X is a BMP-$_2$ receptor binding amino acid sequence having the sequence AISMLYLDEKVVL (SEQ ID NO:7) wherein SEQ ID NO:7 was stepwise synthesized in parallel from $R_2$ trifunctional amino acids of formula I when $R_3$ is 0 backbone atoms and each $R_2$ is lysine. The resulting synthetic growth modulator analog is of the following specific structure:

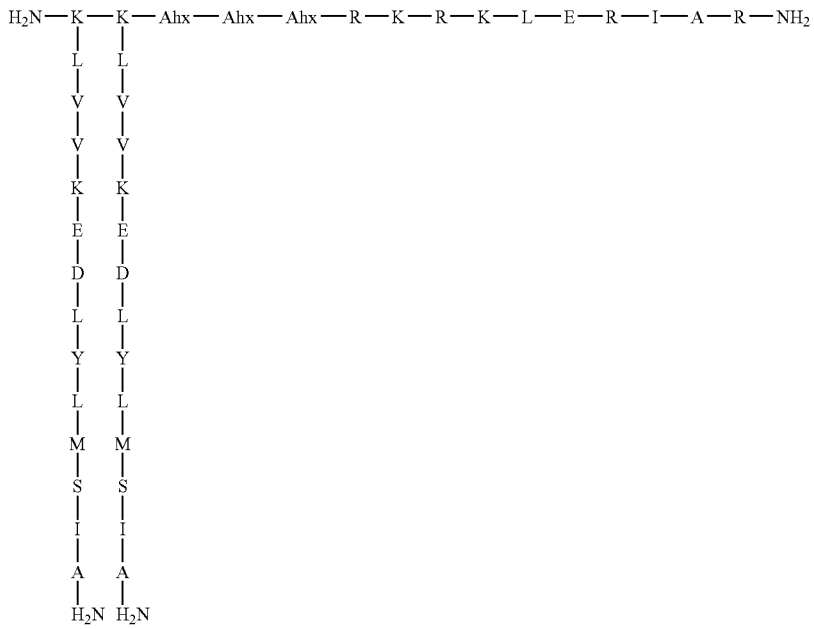

and is sometimes called B2A2-K2-NS. In the foregoing structure, "Ahx" is 6-amino hexanoic acid, sometimes also called "6-Ahx" or "Hex". The single letters are standard amino acid single letter abbreviations for the naturally coded amino acids.

EXAMPLE 24

Figure 12:
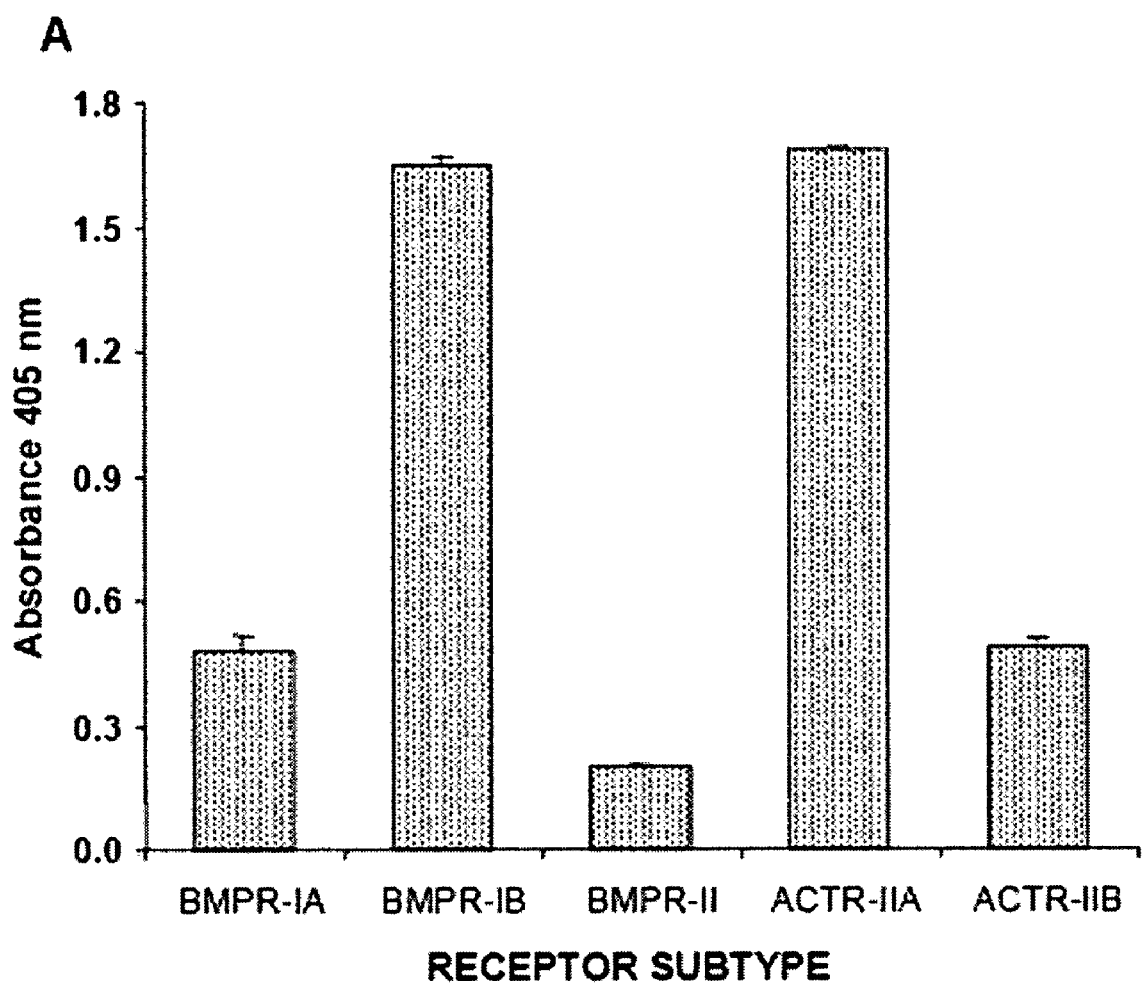
FIG. 12 is a graph illustrating the specific binding between a compound of the present invention and BMP-2 Receptor.
Figure 13:
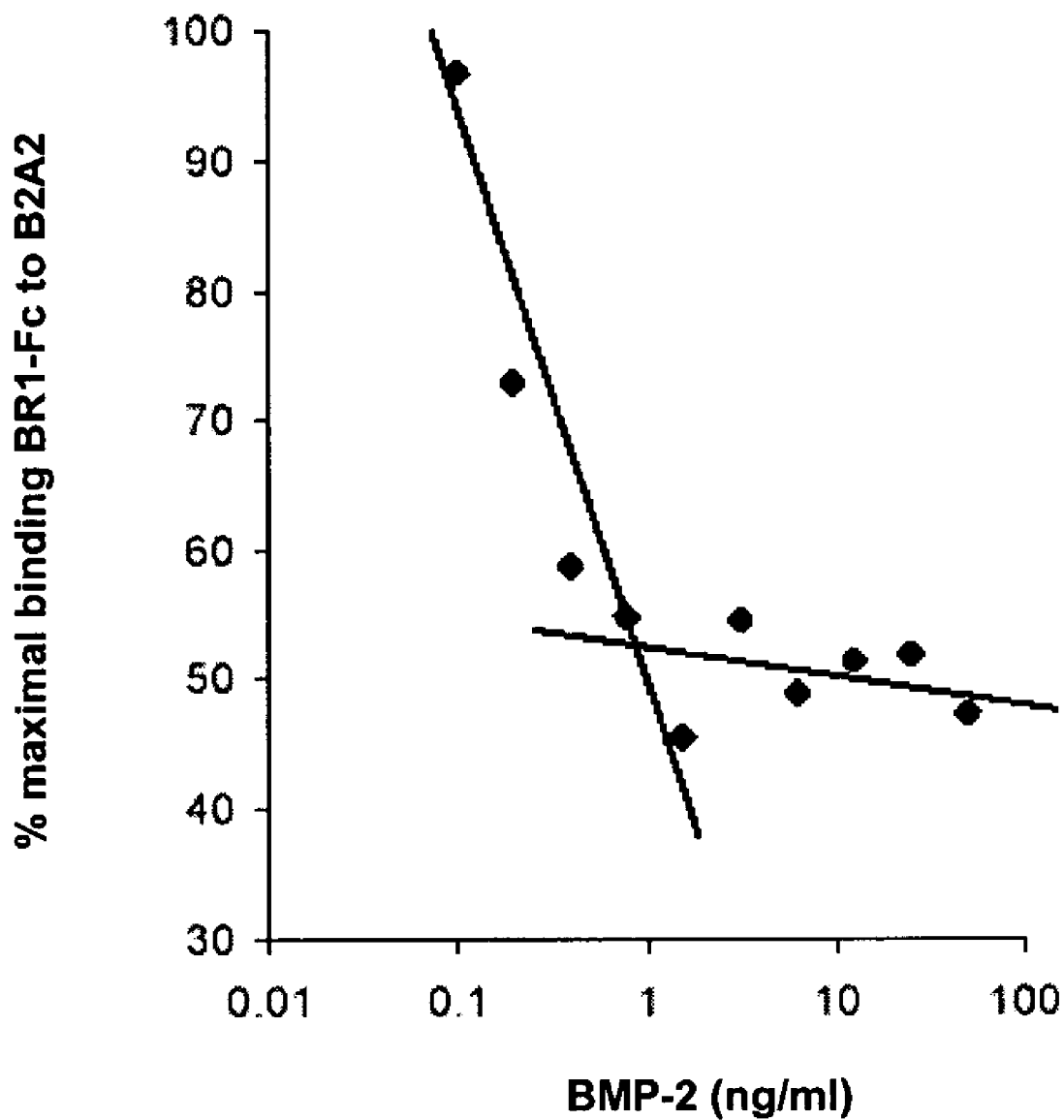
FIG. 13 is a graph illustrating the synergistic action of BMP-2 and B2A2 binding to BMP-2 receptor.

The compound of Example 2 was tested for specific binding to Bone Morphogenic Protein-2 receptors. Referring now to FIG. 12, results of solid phase receptor binding assays utilizing purified receptor/Fc chimeric molecules are illustrated. The chimeras are recombinant constructs of the soluble ectodomain of various receptor molecules (BMPR and ActivinR isoforms) fused to the carboxyl-terminal of the human IgG1 Fc region via a polypeptide liner. ELISA plates were coated with B2A2 or control compounds, soluble chimeric receptor/Fc antibody and quantified with a colorimeteric ELISA. B2A2 was shown to bind preferentially to BMPR-Ib and ActivinR-II, as well as other isoforms in the following order: BMPR-Ib=ActR-II>>BMPR-Ia=ActRIIb>BMPR-II. Insulin, used as a control, did not bind either B2A2 or BMP-2 (data not shown). Referring now to FIG. 13, B2A2 binding to purified BMP-2 receptor/Fc chimeric molecules in varying concentrations of BMP-2 is illustrated. BMP-2 added in large molar excess with the receptors blocked binding to B2A2. When BMP-2 was added in varying concentrations, the resulting displacement curve suggests two-stage binding kinetics of B2A2 to BMPR-Ib.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound of formula:

$$R_1-X-R_6-R_5-Y-Z-R_4$$
$$|$$
$$R_6$$
$$|$$
$$X$$
$$|$$
$$R_1$$

II wherein:

X is a peptide chain that is AISMLYLDENEKVVL (SEQ ID NO: 7);

$R_1$ is independently a hydrogen (H—);

$R_6$ is independently a linker, wherein $R_6$ is a chain of 0 peptide bonds;

$R_5$ is a trifunctional alpha amino acid residue and, wherein X is covalently bonded to when $R_6$ is 0 peptide bonds;

$R_4$ is —NH2;

Y is a linker that is Ahx-Ahx-Ahx, wherein Ahx is 6-amino hexanoic acid; and

Z is RKRLDRIAR (SEQ ID NO: 5).

2. The compound of claim 1 wherein $R_5$ is an L- or D-diamine amino acid residue.

3. The compound of claim 2 wherein the L- or D-diamine amino acid residue is 2,3 diamino propionyl amino acid, 2,4 diamino butylic amino acid, lysine or ornithine.

4. The compound of claim 1 wherein X is covalently bonded to $R_5$ wherein the covalent bonds comprise an amide, disulfide, thioether, Schiff base, reduced Schiff base, imide, secondary amine, carbonyl, urea, hydrazone or oxime bond.

5. A compound having the following structure:

H₂N—A—I—S—M—L—Y—L—D—E—K—V—V—L—K—Ahx—Ahx—Ahx—R—K—R—K—L—E—R—I—A—R—NH₂
                                              |
                                              L
                                              |
                                              V
                                              |
                                              V
                                              |
                                              K
                                              |
                                              E
                                              |
                                              D
                                              |
                                              L
                                              |
                                              Y
                                              |
                                              L
                                              |
                                              M
                                              |
                                              S
                                              |
                                              I
                                              |
                                              A
                                              |
                                              H₂N wherein Ahx is 6-amino hexanoic acid.

6. A bioactive implant having at least one coating comprising the compound of claim 1.

7. A pharmaceutical composition comprising the compound of claim 1 or a pharmaceutically acceptable salt thereof and a pharmaceutical carrier.

8. The pharmaceutical composition of claim 7 further comprising a Bone Morphogenic Protein-2.

* * * * *

UNITED STATES PATENT AND TRADEMARK OFFICE
CERTIFICATE OF CORRECTION

PATENT NO. : 7,482,427 B2  Page 1 of 4
APPLICATION NO. : 11/064039
DATED : January 27, 2009
INVENTOR(S) : Paul O. Zamora et al.

It is certified that error appears in the above-identified patent and that said Letters Patent is hereby corrected as shown below:

Col. 6, line 11, is replaced as shown:

about 15 backbone atoms covalently bonded to $R_5$ when

Col. 6, line 14, is replaced as shown:

covalently bonded through a side chain of $R_5$

Col. 15, line 17, is replaced as shown:

```
H2N—K-K-Ahx-Ahx-Ahx-R-K-R-K-L-E-R-I-A-R—NH2
     |  |
     A  A
     |  |
     I  I
     |  |
     S  S
     |  |
     M  M
     |  |
     L  L
     |  |
     Y  Y
     |  |
     L  L
     |  |
     D  D
     |  |
     E  E
     |  |
     N  N
     |  |
     E  E
     |  |
     K  K
     |  |
     V  V
     |  |
     V  V
     |  |
     L  L
     |  |
    NH2 NH2
```

Col. 23, line 10, is replaced as shown:

sequence having the sequence AISMLYLDENEKVVL (SEQ ID

Signed and Sealed this

Eighth Day of June, 2010

David J. Kappos
*Director of the United States Patent and Trademark Office*

Col. 23, line 16, is replaced as shown:

```
H2N—K-K-Ahx-Ahx-Ahx-R-K-R-K-L-E-R-I-A-R—NH2
     |   |
     L   L
     -   -
     V   V
     -   -
     V   V
     -   -
     K   K
     -   -
     E   E
     -   -
     N   N
     -   -
     E   E
     -   -
     D   D
     -   -
     L   L
     -   -
     Y   Y
     -   -
     L   L
     -   -
     M   M
     -   -
     S   S
     -   -
     I   I
     -   -
     A   A
     —   —
     NH2 NH2
```

Col. 26, line 62, is replaced as shown:

sequence having the sequence AISMLYLDENEKVVL

Col. 26, line 65, is replaced as shown:

when $R_6$ is lysine and $R_5$ is lysine. The resulting

Col. 27, lines 1-23, are replaced as shown:

```
H2N—A-I-S-M-L-Y-L-D-E-N-E-K-V-V-L-K-K-Ahx-Ahx-Ahx-R-K-R-L-D-R-I-A-R—NH2
                                    |
                                    K
                                    -
                                    L
                                    -
                                    V
                                    -
                                    V
                                    -
                                    K
                                    -
                                    E
                                    -
                                    N
                                    -
                                    E
                                    -
                                    D
                                    -
                                    L
                                    -
                                    Y
                                    -
                                    L
                                    -
                                    M
                                    -
                                    S
                                    -
                                    I
                                    -
                                    A
                                    —
                                    H2N
```

CERTIFICATE OF CORRECTION (continued)
U.S. Pat. No. 7,482,427 B2

Col. 27, line 30, is replaced as shown:

theoretical molecular weight of B2A2-K-NS is 5344

Col. 38, line 1, is replaced as shown:

sequence having the sequence AISMLYLDENEKVVL (SEQ ID

Col. 39, line 1, is replaced as shown:

```
H2N—K-K-Ahx-Ahx-Ahx-R-K-R-K-L-E-R-I-A-R—NH2
      |  |
      |  L-V-V-K-E-N-E-D-L-Y-L-M-S-I-A—NH2
      L-V-V-K-E-N-E-D-L-Y-L-M-S-I-A—NH2
```

Col. 58, line 33, is replaced as shown:

```
NH2—A-I-S-M-L-Y-L-D-E-N-E-K-V-V-L-K-Ahx-Ahx-Ahx-R-K-R-K-L-E-R-I-A-R—NH2
                                    |
                                    L-V-V-K-E-N-E-D-L-Y-L-M-S-I-A—NH2
```

Claim 5 structure, is replaced as shown:

H₂N—A-I-S-M-L-Y-L-D-E-K-V-V-L-K-Ahx-Ahx-Ahx-R-K-R-L-D-R-I-A-R—NH₂
|
H₂N—A-I-S-M-L-Y-L-D-E-N-E-K-V-V-L—

UNITED STATES PATENT AND TRADEMARK OFFICE
CERTIFICATE OF CORRECTION

PATENT NO. : 7,482,427 B2  
APPLICATION NO. : 11/064039  
DATED : January 27, 2009  
INVENTOR(S) : Paul O. Zamora et al.

Page 1 of 1

It is certified that error appears in the above-identified patent and that said Letters Patent is hereby corrected as shown below:

In the specification

Column 26, line 65 should read:

-- when $R_6$ is 0 backbone atoms and $R_5$ is lysine. The resulting --

The structure at column 27, lines 1-23 should have the following structure:

$$H_2N\text{-}A\text{-}I\text{-}S\text{-}M\text{-}L\text{-}Y\text{-}L\text{-}D\text{-}E\text{-}N\text{-}E\text{-}K\text{-}V\text{-}V\text{-}L\text{-}K\text{-}Ahx\text{-}Ahx\text{-}Ahx\text{-}R\text{-}K\text{-}R\text{-}K\text{-}L\text{-}E\text{-}R\text{-}I\text{-}A\text{-}R\text{-}NH_2$$

with a branch at K going to: L-V-V-K-E-N-E-D-L-Y-L-M-S-I-A-N$_2$H (read as $H_2N\text{-}A\text{-}I\text{-}S\text{-}M\text{-}L\text{-}Y\text{-}L\text{-}D\text{-}E\text{-}N\text{-}E\text{-}K\text{-}V\text{-}V\text{-}L$)

Column 27, line 30, should read:

-- theoretical molecular weight of B2A2-K-NS is 5486.9. --

Signed and Sealed this  
Eighth Day of December, 2015

Michelle K. Lee  
*Director of the United States Patent and Trademark Office*

SEQUENCE LISTING

<160> NUMBER OF SEQ ID NOS: 44

<210> SEQ ID NO 1
<211> LENGTH: 6
<212> TYPE: PRT
<213> ORGANISM: Artificial
<220> FEATURE:
<223> OTHER INFORMATION: heparin-binding motif
<220> FEATURE:
<221> NAME/KEY: MISC_FEATURE
<222> LOCATION: (1)..(3)
<223> OTHER INFORMATION: where each Xaa is independently lysine or
      arginine
<220> FEATURE:

```
<221> NAME/KEY: MISC_FEATURE
<222> LOCATION: (4)..(5)
<223> OTHER INFORMATION: where each Xaa is independently any amino acid
<220> FEATURE:
<221> NAME/KEY: MISC_FEATURE
<222> LOCATION: (6)..(6)
<223> OTHER INFORMATION: where Xaa is lysine or arginine

<400> SEQUENCE: 1

Xaa Xaa Xaa Xaa Xaa Xaa
1               5

<210> SEQ ID NO 2
<211> LENGTH: 10
<212> TYPE: PRT
<213> ORGANISM: Artificial
<220> FEATURE:
<223> OTHER INFORMATION: synthetic heparin-binding sequence

<400> SEQUENCE: 2

Arg Lys Arg Lys Leu Glu Arg Ile Ala Arg
1               5                   10

<210> SEQ ID NO 3
<211> LENGTH: 10
<212> TYPE: PRT
<213> ORGANISM: Artificial
<220> FEATURE:
<223> OTHER INFORMATION: synthetic heparin-binding sequence

<400> SEQUENCE: 3

Arg Lys Arg Lys Leu Gly Arg Ile Ala Arg
1               5                   10

<210> SEQ ID NO 4
<211> LENGTH: 10
<212> TYPE: PRT
<213> ORGANISM: Artificial
<220> FEATURE:
<223> OTHER INFORMATION: synthetic heparin-binding sequence

<400> SEQUENCE: 4

Arg Lys Arg Lys Leu Trp Arg Ala Arg Ala
1               5                   10

<210> SEQ ID NO 5
<211> LENGTH: 9
<212> TYPE: PRT
<213> ORGANISM: Artificial
<220> FEATURE:
<223> OTHER INFORMATION: synthetic heparin-binding sequence

<400> SEQUENCE: 5

Arg Lys Arg Leu Asp Arg Ile Ala Arg
1               5

<210> SEQ ID NO 6
<211> LENGTH: 11
<212> TYPE: PRT
<213> ORGANISM: Artificial
<220> FEATURE:
<223> OTHER INFORMATION: synthetic heparin-binding sequence

<400> SEQUENCE: 6

Arg Lys Arg Lys Leu Glu Arg Ile Ala Arg Cys
1               5                   10
```

```
<210> SEQ ID NO 7
<211> LENGTH: 15
<212> TYPE: PRT
<213> ORGANISM: Artificial
<220> FEATURE:
<223> OTHER INFORMATION: synthetic BMP-2 analog

<400> SEQUENCE: 7

Ala Ile Ser Met Leu Tyr Leu Asp Glu Asn Glu Lys Val Val Leu
1               5                   10                  15

<210> SEQ ID NO 8
<211> LENGTH: 17
<212> TYPE: PRT
<213> ORGANISM: Artificial
<220> FEATURE:
<223> OTHER INFORMATION: synthetic BMP-2 analog

<400> SEQUENCE: 8

Ile Ser Met Leu Tyr Leu Asp Glu Asn Glu Lys Val Val Leu Lys Asn
1               5                   10                  15

Tyr

<210> SEQ ID NO 9
<211> LENGTH: 13
<212> TYPE: PRT
<213> ORGANISM: Artificial
<220> FEATURE:
<223> OTHER INFORMATION: synthetic BMP-7 analog

<400> SEQUENCE: 9

Leu Tyr Phe Asp Glu Ser Ser Asn Val Ile Leu Lys Lys
1               5                   10

<210> SEQ ID NO 10
<211> LENGTH: 13
<212> TYPE: PRT
<213> ORGANISM: Artificial
<220> FEATURE:
<223> OTHER INFORMATION: synthetic BMP-2 analog

<400> SEQUENCE: 10

Leu Tyr Val Asp Phe Ser Asp Val Gly Trp Asn Asp Trp
1               5                   10

<210> SEQ ID NO 11
<211> LENGTH: 15
<212> TYPE: PRT
<213> ORGANISM: Artificial
<220> FEATURE:
<223> OTHER INFORMATION: synthetic BMP-2 analog

<400> SEQUENCE: 11

Glu Lys Val Val Leu Lys Asn Tyr Gln Asp Met Val Val Glu Gly
1               5                   10                  15

<210> SEQ ID NO 12
<211> LENGTH: 16
<212> TYPE: PRT
<213> ORGANISM: Artificial
<220> FEATURE:
<223> OTHER INFORMATION: synthetic BMP-2 analog

<400> SEQUENCE: 12

Cys Ala Ile Ser Met Leu Tyr Leu Asp Glu Asn Glu Lys Val Val Leu
1               5                   10                  15
```

-continued

```
<210> SEQ ID NO 13
<211> LENGTH: 16
<212> TYPE: PRT
<213> ORGANISM: Artificial
<220> FEATURE:
<223> OTHER INFORMATION: synthetic BMP-2 analog

<400> SEQUENCE: 13

Ala Phe Tyr Cys His Gly Glu Cys Pro Phe Pro Leu Ala Asp His Leu
1 5 10 15

<210> SEQ ID NO 14
<211> LENGTH: 23
<212> TYPE: PRT
<213> ORGANISM: Artificial
<220> FEATURE:
<223> OTHER INFORMATION: synthetic BMP-2 analog

<400> SEQUENCE: 14

Pro Phe Pro Leu Ala Asp His Leu Asn Ser Thr Asn His Ala Ile Val
1 5 10 15

Gln Thr Leu Val Asn Ser Val
20

<210> SEQ ID NO 15
<211> LENGTH: 15
<212> TYPE: PRT
<213> ORGANISM: Artificial
<220> FEATURE:
<223> OTHER INFORMATION: synthetic reverse BMP-2 analog

<400> SEQUENCE: 15

Leu Val Val Lys Glu Asn Glu Asp Leu Tyr Leu Met Ser Ile Ala
1 5 10 15

<210> SEQ ID NO 16
<211> LENGTH: 17
<212> TYPE: PRT
<213> ORGANISM: Artificial
<220> FEATURE:
<223> OTHER INFORMATION: synthetic reverse BMP-2 analog

<400> SEQUENCE: 16

Tyr Asn Lys Leu Val Val Lys Glu Asn Glu Asp Leu Tyr Leu Met Ser
1 5 10 15

Ile

<210> SEQ ID NO 17
<211> LENGTH: 13
<212> TYPE: PRT
<213> ORGANISM: Artificial
<220> FEATURE:
<223> OTHER INFORMATION: synthetic reverse BMP-2 analog

<400> SEQUENCE: 17

Lys Lys Leu Ile Val Asn Ser Ser Glu Asp Phe Tyr Leu
1 5 10

<210> SEQ ID NO 18
<211> LENGTH: 13
<212> TYPE: PRT
<213> ORGANISM: Artificial
<220> FEATURE:
<223> OTHER INFORMATION: synthetic reverse BMP-7 analog

<400> SEQUENCE: 18

```
Trp Asp Asn Trp Gly Val Asp Ser Phe Asp Val Tyr Leu
1               5                   10
```

<210> SEQ ID NO 19
<211> LENGTH: 15
<212> TYPE: PRT
<213> ORGANISM: Artificial
<220> FEATURE:
<223> OTHER INFORMATION: synthetic reverse BMP-2 analog

<400> SEQUENCE: 19

```
Gly Glu Val Val Met Asp Gln Tyr Asn Lys Leu Val Val Lys Glu
1               5                   10                  15
```

<210> SEQ ID NO 20
<211> LENGTH: 16
<212> TYPE: PRT
<213> ORGANISM: Artificial
<220> FEATURE:
<223> OTHER INFORMATION: synthetic reverse BMP-2 analog

<400> SEQUENCE: 20

```
Leu His Asp Ala Leu Pro Phe Pro Cys Glu Gly His Cys Tyr Phe Ala
1               5                   10                  15
```

<210> SEQ ID NO 21
<211> LENGTH: 23
<212> TYPE: PRT
<213> ORGANISM: Artificial
<220> FEATURE:
<223> OTHER INFORMATION: synthetic reverse BMP-2 analog

<400> SEQUENCE: 21

```
Val Ser Asn Val Leu Thr Gln Val Ile Ala His Asn Thr Ser Asn Leu
1               5                   10                  15

His Asp Ala Leu Pro Phe Pro
            20
```

<210> SEQ ID NO 22
<211> LENGTH: 16
<212> TYPE: PRT
<213> ORGANISM: Artificial
<220> FEATURE:
<223> OTHER INFORMATION: synthetic reverse BMP-2 analog

<400> SEQUENCE: 22

```
Leu Val Val Lys Glu Asn Glu Asp Leu Tyr Leu Met Ser Ile Ala Cys
1               5                   10                  15
```

<210> SEQ ID NO 23
<211> LENGTH: 21
<212> TYPE: PRT
<213> ORGANISM: Artificial
<220> FEATURE:
<223> OTHER INFORMATION: synthetic TGF-beta1 analog

<400> SEQUENCE: 23

```
Ile Val Tyr Tyr Val Gly Arg Lys Pro Lys Val Glu Gln Leu Ser Asn
1               5                   10                  15

Met Ile Val Arg Ser
            20
```

<210> SEQ ID NO 24
<211> LENGTH: 22
<212> TYPE: PRT

```
<213> ORGANISM: Artificial
<220> FEATURE:
<223> OTHER INFORMATION: synthetic TGF-beta2 analog

<400> SEQUENCE: 24

Thr

```
<212> TYPE: PRT
<213> ORGANISM: Artificial
<220> FEATURE:
<223> OTHER INFORMATION: synthetic BMP-4 analog

<400> SEQUENCE: 29

Ala Ile Ser Met Leu Tyr Leu Asp Glu Tyr Asp Lys Val Val Leu Lys
1               5                   10                  15

Asn Tyr Gln Glu Met Val Val
            20

<210> SEQ ID NO 30
<211> LENGTH: 23
<212> TYPE: PRT
<213> ORGANISM: Artificial
<220> FEATURE:
<223> OTHER INFORMATION: synthetic BMP-5 analog

<400> SEQUENCE: 30

Ala Ile Ser Val Leu Tyr Phe Asp Asp Ser Ser Asn Val Ile Leu Lys
1               5                   10                  15

Lys Tyr Arg Asn Met Val Val
            20

<210> SEQ ID NO 31
<211> LENGTH: 23
<212> TYPE: PRT
<213> ORGANISM: Artificial
<220> FEATURE:
<223> OTHER INFORMATION: synthetic BMP-6 analog

<400> SEQUENCE: 31

Ala Ile Ser Val Leu Tyr Phe Asp Asp Asn Ser Asn Val Ile Leu Lys
1               5                   10                  15

Lys Tyr Arg Asn Met Val Val
            20

<210> SEQ ID NO 32
<211> LENGTH: 23
<212> TYPE: PRT
<213> ORGANISM: Artificial
<220> FEATURE:
<223> OTHER INFORMATION: synthetic BMP-7 analog

<400> SEQUENCE: 32

Ala Ile Ser Val Leu Tyr Phe Asp Asp Ser Ser Asn Val Ile Leu Lys
1               5                   10                  15

Lys Tyr Arg Asn Met Val Val
            20

<210> SEQ ID NO 33
<211> LENGTH: 23
<212> TYPE: PRT
<213> ORGANISM: Artificial
<220> FEATURE:
<223> OTHER INFORMATION: synthetic BMP-8 analog

<400> SEQUENCE: 33

Ala Thr Ser Val Leu Tyr Tyr Asp Ser Ser Asn Asn Val Ile Leu Arg
1               5                   10                  15

Lys Ala Arg Asn Met Val Val
            20

<210> SEQ ID NO 34
```

```
<211> LENGTH: 23
<212> TYPE: PRT
<213> ORGANISM: Artificial
<220> FEATURE:
<223> OTHER INFORMATION: synthetic BMP-9 analog

<400> SEQUENCE: 34

Ile Ser Val Leu Tyr Lys Asp Asp Met Gly Val Pro Thr Leu Lys Tyr
1               5                   10                  15

His Tyr Glu Gly Met Ser Val
            20

<210> SEQ ID NO 35
<211> LENGTH: 22
<212> TYPE: PRT
<213> ORGANISM: Artificial
<220> FEATURE:
<223> OTHER INFORMATION: synthetic BMP-10 analog

<400> SEQUENCE: 35

Ile Ser Ile Leu Tyr Leu Asp Lys Gly Val Val Thr Tyr Lys Phe Lys
1               5                   10                  15

Tyr Glu Gly Met Ala Val
            20

<210> SEQ ID NO 36
<211> LENGTH: 22
<212> TYPE: PRT
<213> ORGANISM: Artificial
<220> FEATURE:
<223> OTHER INFORMATION: synthetic BMP-11 analog

<400> SEQUENCE: 36

Ile Asn Met Leu Tyr Phe Asn Asp Lys Gln Gln Ile Ile Tyr Gly Lys
1               5                   10                  15

Ile Pro Gly Met Val Val
            20

<210> SEQ ID NO 37
<211> LENGTH: 22
<212> TYPE: PRT
<213> ORGANISM: Artificial
<220> FEATURE:
<223> OTHER INFORMATION: synthetic BMP-12 analog

<400> SEQUENCE: 37

Ile Ser Ile Leu Tyr Ile Asp Ala Ala Asn Asn Val Val Tyr Lys Gln
1               5                   10                  15

Tyr Glu Asp Met Val Val
            20

<210> SEQ ID NO 38
<211> LENGTH: 22
<212> TYPE: PRT
<213> ORGANISM: Artificial
<220> FEATURE:
<223> OTHER INFORMATION: synthetic BMP-13 analog

<400> SEQUENCE: 38

Ile Ser Ile Leu Tyr Ile Asp Ala Gly Asn Asn Val Val Tyr Lys Gln
1               5                   10                  15

Tyr Glu Asp Met Val Val
            20
```

```
<210> SEQ ID NO 39
<211> LENGTH: 22
<212> TYPE: PRT
<213> ORGANISM: Artificial
<220> FEATURE:
<223> OTHER INFORMATION: synthetic BMP-14 analog

<400> SEQUENCE: 39

Ile Ser Ile Leu Phe Ile Asp Ser Ala Asn Asn Val Val Tyr Lys Gln
1               5                   10                  15

Tyr Glu Asp Met Val Val
            20

<210> SEQ ID NO 40
<211> LENGTH: 22
<212> TYPE: PRT
<213> ORGANISM: Artificial
<220> FEATURE:
<223> OTHER INFORMATION: synthetic BMP-15 analog

<400> SEQUENCE: 40

Ile Ser Val Leu Met Ile Glu Ala Asn Gly Ser Ile Leu Tyr Lys Glu
1               5                   10                  15

Tyr Glu Gly Met Ile Ala
            20

<210> SEQ ID NO 41
<211> LENGTH: 22
<212> TYPE: PRT
<213> ORGANISM: Artificial
<220> FEATURE:
<223> OTHER INFORMATION: synthetic GDF-1 analog

<400> SEQUENCE: 41

Ile Ser Val Leu Phe Phe Asp Asn Ser Asp Asn Val Val Leu Arg Gln
1               5                   10                  15

Tyr Glu Asp Met Val Val
            20

<210> SEQ ID NO 42
<211> LENGTH: 22
<212> TYPE: PRT
<213> ORGANISM: Artificial
<220> FEATURE:
<223> OTHER INFORMATION: synthetic GDF-3 analog

<400> SEQUENCE: 42

Ile Ser Met Leu Tyr Gln Asp Asn Asn Asp Asn Val Ile Leu Arg His
1               5                   10                  15

Tyr Glu Asp Met Val Val
            20

<210> SEQ ID NO 43
<211> LENGTH: 22
<212> TYPE: PRT
<213> ORGANISM: Artificial
<220> FEATURE:
<223> OTHER INFORMATION: synthetic GDF-8 analog

<400> SEQUENCE: 43

Ile Asn Met Tyr Leu Phe Asn Gly Lys Glu Gln Ile Ile Tyr Gly Lys
1               5                   10                  15

Ile Pro Ala Met Val Val
            20
```

```
-continued

<210> SEQ ID NO 44
<211> LENGTH: 22
<212> TYPE: PRT
<213> ORGANISM: Artificial
<220> FEATURE:
<223> OTHER INFORMATION: synthetic GDF-9 analog

<400> SEQUENCE: 44

Leu Ser Val Leu Thr Ile Glu Pro Asp Gly Ser Ile Ala Tyr Lys Glu
1               5                   10                  15

Tyr Glu Asp Met Ile Ala
            20
```